United States Patent
Badr

(10) Patent No.: US 11,617,549 B1
(45) Date of Patent: Apr. 4, 2023

(54) MAGNETIC GUIDE FOR INTRAORAL RADIOGRAPHY PRECISION

(71) Applicant: King Abdulaziz University, Jeddah (SA)

(72) Inventor: Fatma Fayez Badr, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/677,289

(22) Filed: Feb. 22, 2022

(51) Int. Cl.
*A61B 6/14* (2006.01)
*A61B 6/06* (2006.01)
*A61B 6/00* (2006.01)
*A61B 50/20* (2016.01)

(52) U.S. Cl.
CPC ............... *A61B 6/145* (2013.01); *A61B 6/06* (2013.01); *A61B 6/4233* (2013.01); *A61B 6/4411* (2013.01); *A61B 2050/21* (2016.02)

(58) Field of Classification Search
None
See application file for complete search history.

(56) References Cited

U.S. PATENT DOCUMENTS

| | | | |
|---|---|---|---|
| 5,513,240 A | 4/1996 | Hausmann et al. | |
| 7,194,064 B2 | 3/2007 | Razzano et al. | |
| 9,314,215 B2 * | 4/2016 | Abramovich | A61B 6/4435 |
| 2003/0073935 A1 * | 4/2003 | Segawa | A61B 5/065 |
| | | | 600/593 |
| 2014/0169533 A1 * | 6/2014 | Razzano | A61B 6/14 |
| | | | 378/205 |
| 2015/0230764 A1 * | 8/2015 | Charnegie | A61B 6/4435 |
| | | | 378/145 |
| 2016/0038105 A1 * | 2/2016 | Hayman | A61B 6/4435 |
| | | | 378/150 |
| 2019/0125048 A1 * | 5/2019 | Altaras | H01F 7/0205 |

FOREIGN PATENT DOCUMENTS

| | | |
|---|---|---|
| CN | 109803586 A | 5/2019 |
| WO | WO 2020/030854 A1 | 2/2020 |

* cited by examiner

*Primary Examiner* — Katherine L Fernandez
(74) *Attorney, Agent, or Firm* — Oblon, McClelland, Maier & Neustadt, L.L.P.

(57) ABSTRACT

A magnetic guide device for intraoral radiography is described. The magnetic guide device comprises a metal rod having a first rod end and a second rod end. The magnetic guide device further comprises a ring slidably attached to the metal rod between the first rod end and the second rod end. The magnetic guide device further comprises a plurality of magnetic attachments. The magnetic guide device further comprises a rectangular collimator attached to the ring by the magnetic attachments. The magnetic guide device further comprises a CMOS sensor. The magnetic guide device further comprises a metal fork having a fork handle slidably attached to the metal rod between the CMOS sensor and the first rod end. The metal fork is configured to hold the CMOS sensor during an intraoral radiography procedure.

13 Claims, 14 Drawing Sheets

MAGNETIC GUIDE FOR INTRAORAL RADIOGRAPHY PRECISION

STATEMENT OF ACKNOWLEDGEMENT

The inventors extend their appreciation to the Deputyship for Research & Innovation, Ministry of Education in Saudi Arabia for funding this research work through the project number X2021-108 and to the support given by King Abdulaziz University, DSR, Jeddah, Saudi Arabia.

BACKGROUND

Technical Field

The present disclosure is directed to intraoral dental radiography; and more particularly to a guide device magnetically supporting components therein, allowing for easy assembly and adjustment thereof, for precise intraoral radiography.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Conventional diagnostic radiography requires an object (to be imaged) to be placed between a radiation source and a detector, and it is further required that relative positions of the radiation source and the detector are aligned to obtain the image. Traditionally, in intraoral (dental) radiography, a cartridge having a piece of radiographic film is placed in the patient's oral cavity, for example behind a patient's tooth, and a radiation beam is projected through the tooth and onto the film. The radiographic film, after being exposed in this manner, is developed in a dark room or a closed processor using special chemicals to obtain a radiographic image of the tooth. More recently, digital techniques have been increasingly employed for dental radiography. In digital dental radiography, an x-ray beam is projected through the patient's teeth in the same manner, but an electronic sensor is placed in the patient's mouth behind the tooth to be examined rather than radiographic film. During the procedure, the technician is required to hold the electronic sensor within the patient's oral cavity. Typically, the technician places the electronic sensor into some type of holder, and then inserts the holder into the oral cavity.

CN109803586A describes an apparatus for imaging teeth including a hinged arm having an x-ray source at one end and an x-ray detector in a detector holder at a second end, with a first collimator disposed near the x-ray source and a second collimator disposed near the x-ray detector. The detector holder is held to the x-ray detector and the second collimator by a series of magnets which are attracted to magnets on the x-ray detector and the second collimator.

WO2020030854A1 describes a wireless intraoral x-ray imaging sensor holder comprising a wireless intraoral x-ray imaging sensor. The holder includes a handle, an x-ray tube alignment ring, and a bite block which includes a bracket part that clips onto a hump of the sensor; specifically, onto a groove provided on the hump of the sensor. The handle is provided with grooves to allow the positioning of the x-ray tube alignment ring to a certain distance from the WIOS. Further, the ring is provided with three separate slides through positions in order to allow for posterior maxillary, bite wing or posterior mandibular imaging position of the sensor.

U.S. Pat. No. 7,194,064B2 describes an apparatus (image capture device) having an x-ray generator, collimator tube, and receptor holder. Receptor holder has a holder end that is operative to hold a digital sensor or x-ray film. Receptor holder can be coupled to collimator tube by magnetism when magnets of collimator tube come into contact with conductor/magnet interface metal snap ring of receptor holder.

Each of the aforementioned references suffers from one or more drawbacks hindering their adoption. For example, CN109803586A does not mention that the x-ray detector and the collimator are supported on a single member (like an elongate member or the like), or particularly any arrangement which allows for convenient adjustment (such as, by sliding) of relative positions of the x-ray detector and the collimator. WO2020030854A1 describes a sensor attached to a bracket by clipping onto a groove provided on a hump of the sensor, but this may require some dexterity and force on part of the technician assembling such device. Moreover, the ring must be provided with three separate slide through positions to allow for adjustment of the sensor, which is tedious for the technician to change for each new image. U.S. Pat. No. 7,194,064B2 does not mention a structure to support the receptor holder and the collimator tube which can allow for convenient adjustment (such as, by sliding) of relative positions thereof. Moreover, the receptor holder is not particularly suitable for holding sensors of different sizes and/or shapes. In general, the existing digital dental devices do not have adequate universal structure for proper positioning of the sensor within the patient's mouth, nor do they provide convenient support structure for adjusting relative positions of the sensor and the collimator.

Accordingly, it is an object of the present disclosure to provide a magnetic guide device for intraoral radiography which provides a support member to hold the sensor and an elongate member to allow for convenient adjustment of the relative positions of the sensor and collimator

SUMMARY

In an exemplary embodiment, a magnetic guide device for intraoral radiography is described. The magnetic guide device comprises a metal rod having a first rod end and a second rod end. The magnetic guide device further comprises a ring slidably attached to the metal rod between the first rod end and the second rod end. The magnetic guide device further comprises a plurality of magnetic attachments. The magnetic guide device further comprises a rectangular collimator attached to the ring by the magnetic attachments. The magnetic guide device further comprises a CMOS sensor. The magnetic guide device further comprises a metal fork having a fork handle slidably attached to the metal rod between the CMOS sensor and the first rod end. The metal fork is configured to hold the CMOS sensor during an intraoral radiography procedure.

In some embodiments, the rectangular collimator comprises a front side and a back side. The rectangular collimator further comprises a cylindrical extension on the front side. The rectangular collimator further comprises a rectangular opening which extends through the rectangular collimator from the front side to the back side. The rectangular opening is configured to pass x-rays from the front side to the back side. The rectangular collimator further comprises a magnetic material configured to cover at least a portion of the back side, wherein the portion conforms to a periphery of the rectangular opening.

In some embodiments, the ring comprises a ring handle. The ring further comprises a ring guide comprising a plurality of insert cavities spaced around a periphery of the ring guide. Each insert cavity is configured to receive one of a plurality of magnetic inserts such that each magnetic insert is countersunk into one of the insert cavities.

In some embodiments, each magnetic insert comprises one of a permanent magnet selected from the group comprising a neodymium iron boron (NdFeB) magnet, a samarium cobalt (SmCo) magnet, an alnico magnet, ceramic magnet, and a ferrite magnet; and a magnetic metal selected from the group comprising nickel, cobalt, steel, magnetic stainless steel, barium ferrite, and rare earth metals.

In some embodiments, the magnetic guide device further comprises a plurality of permanent magnets, each permanent magnet having a positive magnetic pole and a negative magnetic pole. Herein, each magnetic attachment contains one of the plurality of permanent magnets. The positive magnetic pole is configured to magnetically bond to the magnetic material and the negative magnetic pole is configured to connect to a respective magnetic insert of the ring.

In some embodiments, the magnetic guide device further comprises a closed cylindrical magnet housing configured to hold one of the permanent magnets. Herein, an outer cylindrical surface of the closed cylindrical magnet housing has a textured surface, a first face of the closed cylindrical magnet housing includes a positive magnetic pole indicator and a second face of the closed cylindrical magnet housing includes a negative magnetic pole indicator.

In some embodiments, the ring handle has a first ring handle end and a second ring handle end. The first ring handle end is connected to the ring guide, and the second ring handle end includes a first channel configured for slidably receiving the metal rod and a second channel configured for receiving a first portion of a wire of the CMOS sensor.

In some embodiments, the fork handle has a first fork handle end and a second fork handle end. The first fork handle end is connected to the metal fork, and the second fork handle end includes a passage configured for slidably receiving the metal rod.

In some embodiments, the magnetic guide device further comprises a plurality of wire guide clips attached to the metal rod between the CMOS sensor and the ring. The plurality of wire guide clips is configured to hold the first portion of the wire parallel to the metal rod.

In some embodiments, the plurality of wire guide clips comprises at least a first wire guide clip, a second wire guide clip and a third wire guide clip. Herein, the first wire guide clip is spaced from the first rod end of the metal rod by a distance $R_1$; the second wire guide clip is spaced from the first rod end of the metal rod by a distance $R_2$; the third wire guide clip is spaced from the first rod end of the metal rod by a distance $R_3$, where $R_1<R_2<R_3$. The third wire guide clip is further configured to stop the ring handle from sliding past the third wire guide clip towards the first rod end.

In some embodiments, the magnetic guide device further comprises a screw having male threads. The screw is configured for insertion through the passage into female threads in the first rod end of the metal rod, such that the metal fork compresses a second portion of the wire between the first wire guide clip and the metal fork.

In some embodiments, the second portion of the wire is perpendicular to the first portion of the wire.

In some embodiments, the metal rod has a square cross section of side length $L_1$ and the passage has a square cross section of side length $L_2$, wherein $L_2=L_1+y$, where $0<y\leq 2$ mm.

In some embodiments, the first channel has a square cross section having side length $L_3$, and the second channel has a round cross section equal of diameter D is selected from a range consisting of 0.1 cm to 0.5 cm.

In some embodiments, the magnetic guide device further comprises a magnetic backing located on the CMOS sensor. The magnetic backing comprises a magnetic material selected from the group comprising a magnetic coating, a magnetic metal sheet, a magnetic tape, and self-adhesive magnetic dots. The magnetic backing is configured to adjustably attract the metal fork by magnetic forces.

In another exemplary embodiment, a method for assembling a magnetic guide device for intraoral radiography is described. The method comprises attaching a CMOS sensor to a metal fork, the CMOS sensor having a wire which extends down a fork handle of the metal fork. The method further comprises inserting a first rod end of a metal rod into a passage in the fork handle of the metal fork. The method further comprises bending the wire by 90 degrees. The method further comprises guiding the wire beneath a plurality of wire guide clips, such that a portion of the wire is parallel to the metal rod. The method further comprises compressing the metal fork against the wire by inserting a screw through the passage into the first rod end. The method further comprises inserting the metal rod into a first channel of a ring handle of a ring. The method further comprises inserting the wire into a second channel of the ring handle of the ring. The method further comprises attaching a magnetic attachment to each of a plurality of magnetic inserts on the ring. The method further comprises magnetically attaching a rectangular collimator to the ring by pressing a back side of the rectangular collimator against the plurality of magnetic attachments.

In some embodiments, the method further comprises attaching each magnetic attachment to one of the magnetic inserts by one of placing a positive magnetic pole of the magnetic attachment against the magnetic insert; and placing a negative magnetic pole of the magnetic attachment against the magnetic insert.

In some embodiments, each magnetic insert has a first magnetic pole; and attaching the magnetic attachment to the magnetic insert comprises placing a second magnetic pole of the magnetic attachment against the first magnetic pole of the magnetic insert, wherein the first magnetic pole and the second magnetic pole are opposite poles.

In another exemplary embodiment, a method for aligning a magnetic guide device for intraoral radiography is described. The method comprises installing a fork handle of a metal fork on a metal rod, the metal fork having tines. The method further comprises attaching a CMOS sensor to the metal fork. The method further comprises aligning the CMOS sensor such that a sensing region of the CMOS sensor is between the tines. The method further comprises installing a ring handle on the metal rod. The method further comprises magnetically attaching a rectangular collimator to a ring guide. The method further comprises aligning the rectangular collimator such that a center of the rectangular collimator is coaxial with a center of the sensing region of the CMOS sensor.

In some embodiments, the method further comprises adjusting a distance between the rectangular collimator and the CMOS sensor by moving the ring handle one of towards the CMOS sensor and away from the CMOS sensor.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
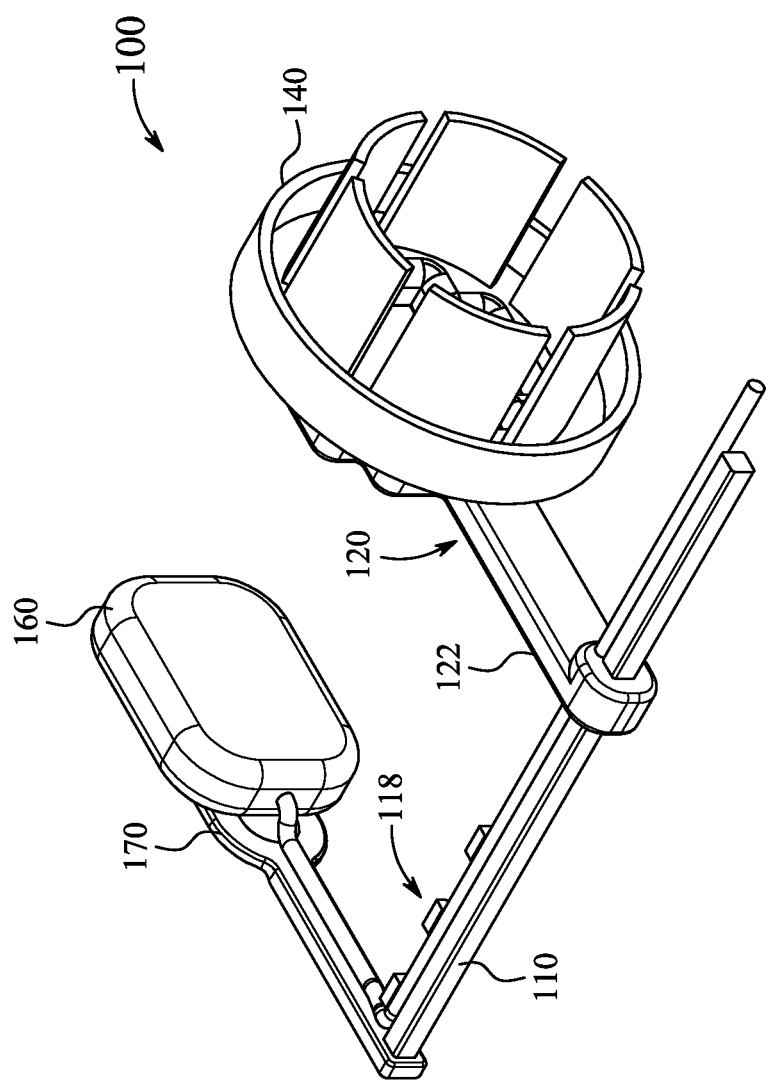
FIG. 1 is an assembled perspective view of a magnetic guide device, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Aspects of this disclosure are directed to a magnetic guide device which provides adjustability through connections between its modular components that are easily snapped together with complementary connection features; and may also allow for using same modular components or different modular components, if needed. The present magnetic guide device requires minimal assembly or adjustment during and/or just prior to actual operation to acquire images. The present magnetic guide device further provides proper alignment of its components, to provide a substantially unobstructed line of sight between a radiation source, such as an existing X-ray emitter, and a CMOS sensor. The magnetic guide device is capable of producing high quality images, which reduces the number of images required to be retaken, thus minimizing exposure of patients to unnecessary radiation.

Figure 2:
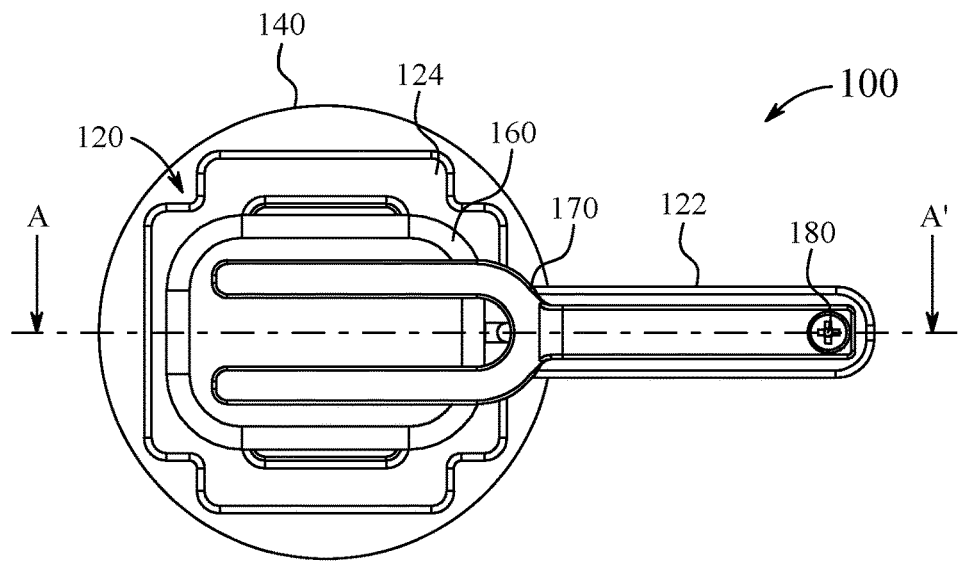
FIG. 2 is a top planar view of the magnetic guide device of FIG. 1, according to certain embodiments.
Figure 3:
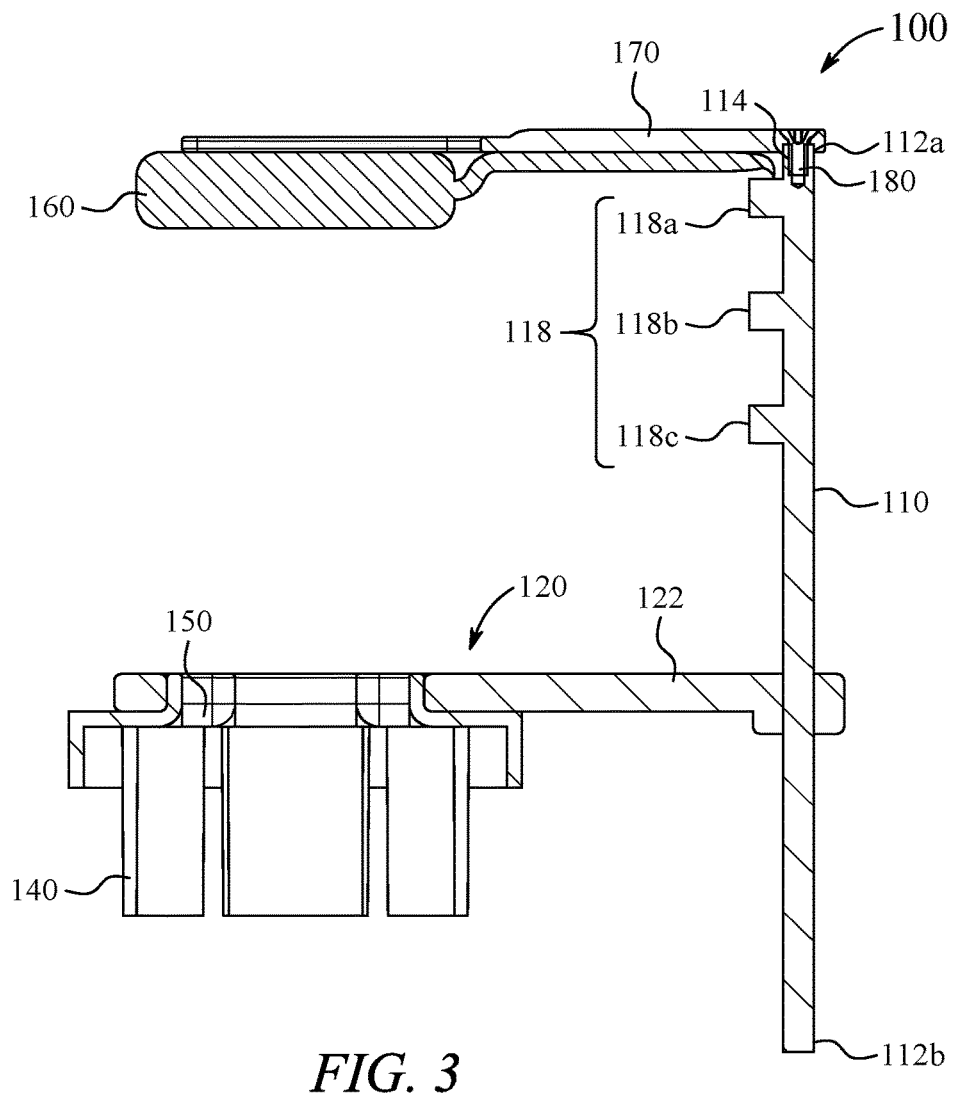
FIG. 3 is a side sectional view of the magnetic guide device taken along a plane AA' of FIG. 2, according to certain embodiments.

Referring to FIG. 1, an assembled view of a magnetic guide device 100 is illustrated. Further, FIG. 2 illustrates a top planar view of the magnetic guide device 100 and FIG. 3 illustrates a sectional side view of the magnetic guide device 100 taken along a plane AA' of FIG. 2. The magnetic guide device 100 of the present disclosure is implemented for intraoral radiography. The magnetic guide device 100 is suitable for use in diagnosis of caries of a tooth, a missing part, lesion, degree of adhesion of tartar, plaque, and a biofilm, and the like in an oral cavity; and may further be suitable for diagnosis of otological regions, treatment and diagnosis of rectal abscess, dermatological diagnosis and the like. Particularly, in intraoral radiography, the present magnetic guide device 100 may be placed inside patient's mouth where it may capture images of the bones, gums, teeth, and any malformations therein. The magnetic guide device 100 of the present disclosure includes separate components, which require minimal assembly or adjustment and which may all cooperate for actual operation to acquire dental and/or medical images. Specifically, the components of the magnetic guide device 100 cooperate to provide a substantially unobstructed line of sight between a radiation source, such as an existing X-ray emitter, and a sensor, such as a CMOS sensor (as described later in the description), supported therein.

As illustrated in FIGS. 1-3, the magnetic guide device 100 includes a metal rod 110 (hereinafter, sometimes referred to as "rod 110"). The rod 110 is in the form of an elongate member onto which other components of the magnetic guide device 100 are supported/mounted, and are thereby aligned to be implemented for intraoral radiography.

Figure 4:
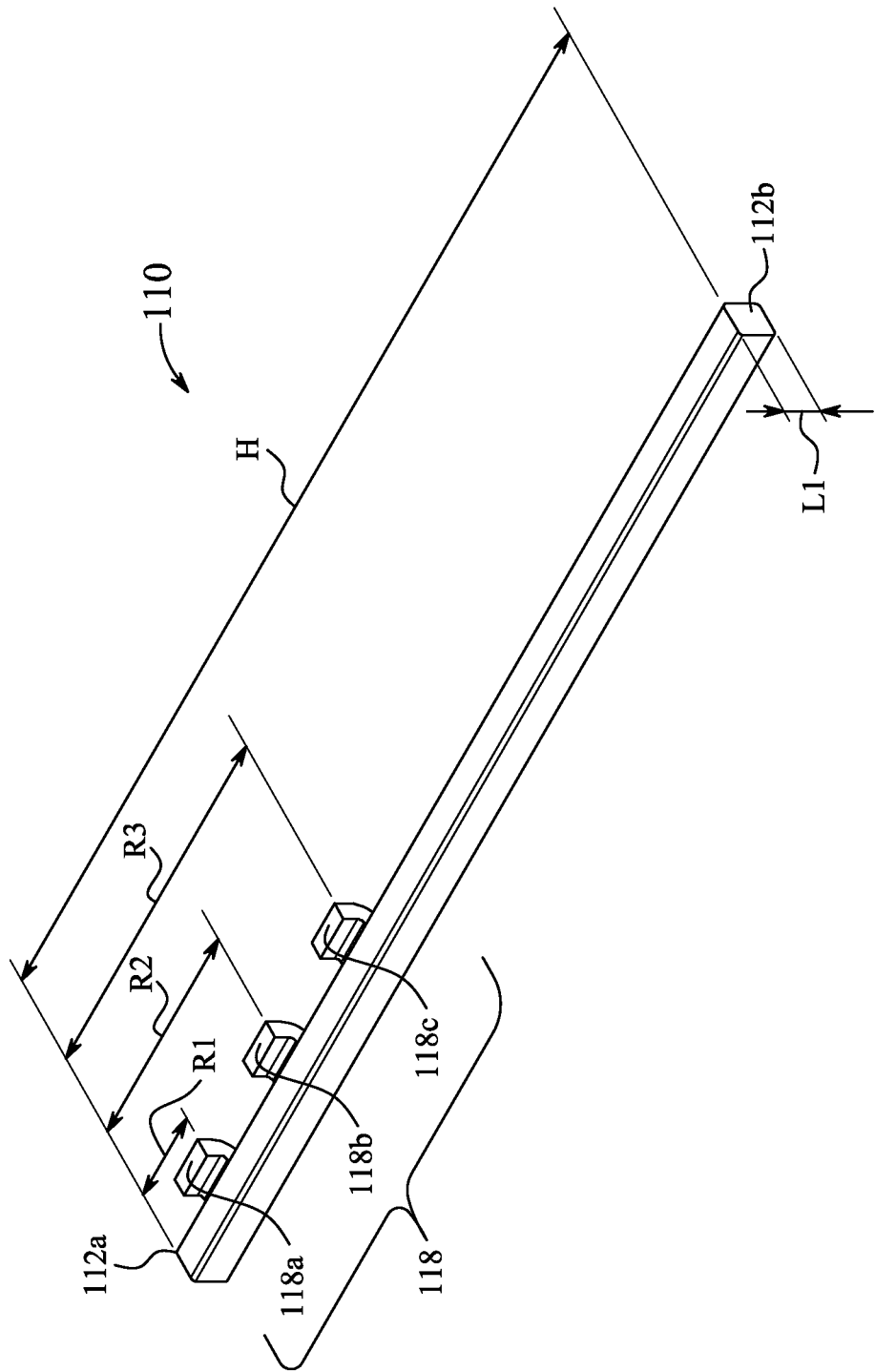
FIG. 4 is a perspective view of a metal rod of the magnetic guide device, according to certain embodiments.

FIG. 4 illustrates a perspective view of the metal rod 110. In the illustrated examples, the rod 110 is shown to have a rectangular, or specifically square shaped cross-section; however, it may be appreciated that the rod 110 may have other suitable cross-sectional profile including, but not limited, to a circular cross-section or a triangular shaped cross-section without departing from the spirit and the scope of the present disclosure. In some other examples, the rod 110 may generally be a flat or planar member without any limitations. It may be appreciated that a length (longitudinal length) and a width of the rod 110 may be sized to allow for properly positioning the magnetic guide device 100 within the patient's oral cavity. In an example, a length 'H' of the rod 110 may be in a range of 12 cm to 18 cm. Further, the rod 110 has a square cross section of side length '$L_1$', which may be in a range of 0.3 cm to 0.6 cm. Also, in the present examples, although the rod 110 has been referred to as "metal rod," implying that the rod 110 is made of metallic material/alloys, such as, stainless steel or the like; however, it may be appreciated that in other examples, the rod 110 may be made of plastic or other suitable material(s) without any limitations.

Further, as illustrated in FIGS. 1-3 in combination and FIG. 4, the rod 110 has a first rod end 112*a* and a second rod end 112*b*. Herein, the first rod end 112*a* and the second rod end 112*b* are longitudinal ends of the rod 110 along the length 'H' thereof. In an aspect of the present disclosure, as particularly illustrated in the FIG. 4, the rod 110 has a hollow cavity 114, in the form of an extruded hole of certain depth, formed at the first rod end 112*a* therein. The hollow cavity 114 is provided with female (internal) threads, and thereby the hollow cavity 114 at the first rod end 112*a* of the rod 110 may be adapted to receive a fastener (as discussed later in description). In an alternative, the metal rod may be configured with threads on the first end without the hollow cavity. In an aspect of the present disclosure, as illustrated, the magnetic guide device 100 further includes a plurality of wire guide clips 118 attached to the metal rod 110. In particular, the plurality of wire guide clips 118 may include at least a first wire guide clip 118*a*, a second wire guide clip 118*b* and a third wire guide clip 118*c*. As shown, the first wire guide clip 118*a* is spaced from the first rod end 112*a* of the metal rod 110 by a distance 'R$_1$'; the second wire guide clip 118*b* is spaced from the first rod end 112*a* of the metal rod 110 by a distance 'R$_2$'; the third wire guide clip 118*c* is spaced from the first rod end 112*a* of the metal rod 110 by a distance 'R$_3$', where R1<R2<R3. In other words, the first wire guide clip 118*a* is closest to the first rod end 112*a* of the metal rod 110; the second wire guide clip 118*b* is relatively farther to the first wire guide clip 118*a* from the first rod end 112*a* of the metal rod 110 and is located between the first wire guide clip 118*a* and the third wire guide clip 118*c*; the third wire guide clip 118*c* is farthest from the first rod end 112*a* of the metal rod 110. Herein, each of the plurality of wire guide clips 118 has a generally L-shaped profile with certain width and is adapted to support a wire or the like therein (as discussed later in the description).

Figure 5A:
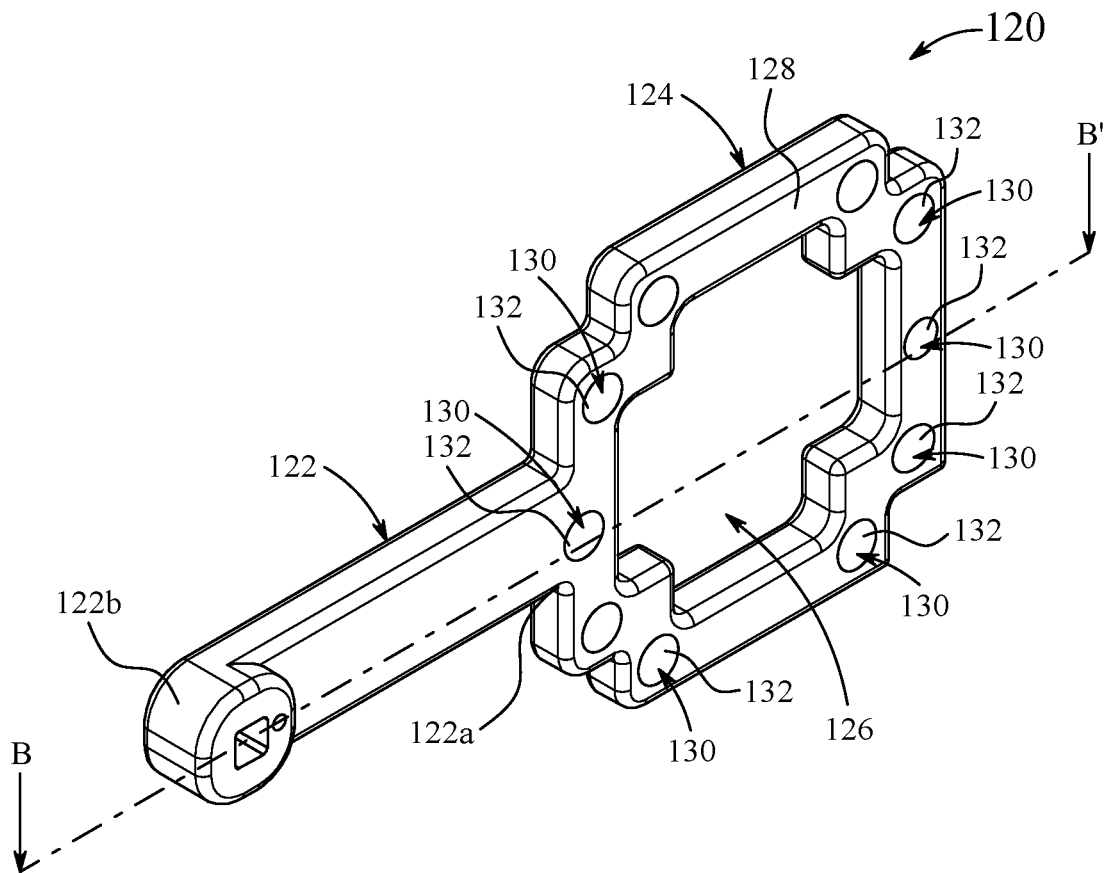
FIG. 5A is a perspective view of a ring of the magnetic guide device, according to certain embodiments.
Figure 5B:
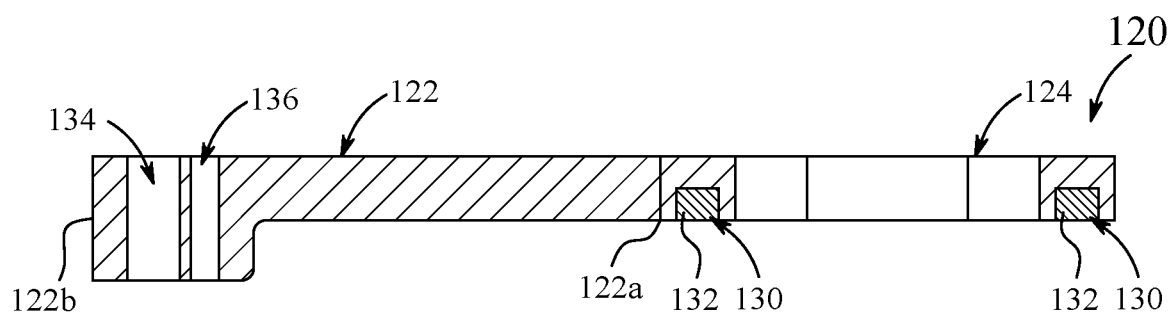
FIG. 5B is a side sectional view of the ring taken along a plane BB' of FIG. 5A, according to certain embodiments.
Figure 5C:
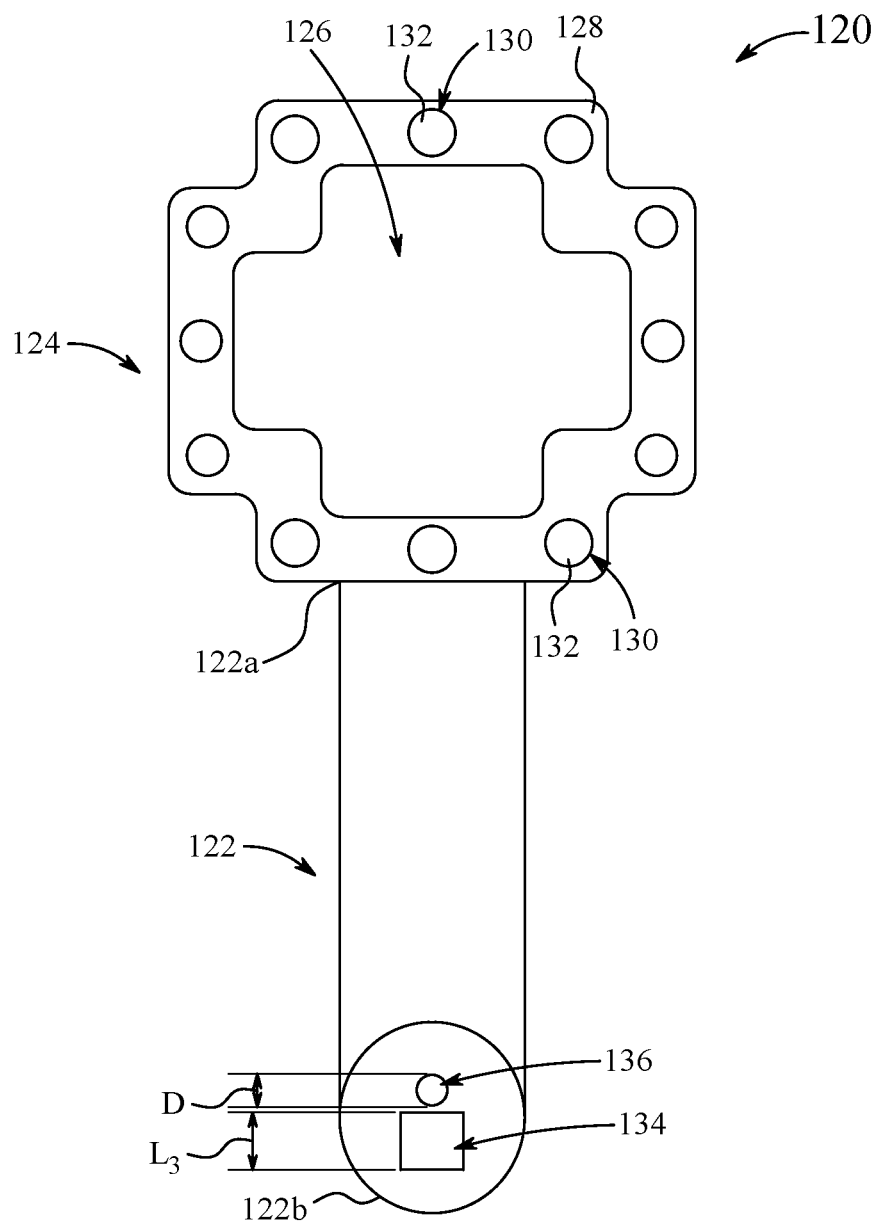
FIG. 5C is a back side planar view of the ring, according to certain embodiments.

Referring to FIGS. 1-3 in combination, as illustrated, the magnetic guide device 100 further includes a ring 120. Further, FIGS. 5A-5C illustrate different views of the ring 120. Herein, the ring 120 is implemented to support one or more components of the magnetic guide device 100. As shown, the ring 120 includes a ring handle 122 and a ring guide 124 affixed to each other. The ring handle 122 has a first ring handle end 122*a* and a second ring handle end 122*b*. The first ring handle end 122*a* is connected to the ring guide 124, to couple the ring handle 122 and the ring guide 124. In one example, the ring 120 may be formed as a unitary member with the ring handle 122 and the ring guide 124 formed together, such as by molding or the like. In other examples, the ring handle 122 and the ring guide 124 may be formed separately and later attached to each other by any suitable attachment methods, such as glue, welding, and the like, to form the ring 120. As may be seen, the ring guide 124 has an opening 126 defined therein. In the illustrated examples, the opening 126 is generally rectangular; and in particular, according to an aspect of the present disclosure, the opening 126 may have a generally cross shape (as shown). Further, as may be seen, the ring guide 124 has a periphery 128 confirming to the shape of the opening 126 with a similar generally cross shape (as better seen in FIG. 5C).

Further, as illustrated, the ring guide 124 includes a plurality of insert cavities (generally represented by reference numeral 130). Herein, each of the insert cavities 130 is in the form of a hollow cylindrical cavity, such as an extruded hole of certain depth. The plurality of insert cavities 130 are spaced in the periphery 128 of the ring guide 124. As shown, the insert cavities 130 are generally located at corners of the periphery 128 of the ring guide 124. In the illustrated examples, the ring guide 124 is shown to include a total of ten insert cavities 130, with eight of the insert cavities 130 grouped into four pairs, and with each such pair of the insert cavities 130 being located at one of the corners of the periphery 128 of the ring guide 124. It may be appreciated that such configuration, including design and number of insert cavities 130 for the ring guide 124, is exemplary only and shall not be construed as limiting to the present disclosure in any manner.

Further, the magnetic guide device 100 includes a plurality of magnetic inserts 132. Herein, each insert cavity 130 is configured to receive one of the plurality of magnetic inserts 132 such that each magnetic insert 132 is countersunk into one of the insert cavities 130. For this purpose, the magnetic inserts 132 are designed to be complementary to the hollow cylindrical shape of the insert cavities 130; that is, each of the magnetic inserts 132 has a cylindrical shape with dimensions equivalent to the hollow cylindrical shape of the insert cavities 130. In an aspect of the present disclosure, each magnetic insert 132 includes one of a permanent magnet selected from the group including a neodymium iron boron (NdFeB) magnet, a samarium cobalt (SmCo) magnet, an alnico magnet, ceramic magnet, and a ferrite magnet; and a magnetic metal selected from the group including nickel, cobalt, steel, magnetic stainless steel, barium ferrite, and rare earth metals. Such configuration for the magnetic insert 132, being either the permanent magnet or the magnetic metal, imparts magnetic properties thereto, to allow the magnetic insert 132 to magnetically connect to another component of the magnetic guide device 100 for its convenient assembly (as discussed later in the description).

Further, as illustrated, in the ring handle 122 of the ring 120, the second ring handle end 122*b* includes a first channel 134 and a second channel 136. Herein, the first channel 134 and the second channel 136 may be in the form of through-hole in the ring handle 122. As best shown in FIG. 5C, the first channel 134 and the second channel 136 are formed in a region which may be carved out from the ring handle 122 proximal to the second ring handle end 122*b* thereof. Further, as shown, the first channel 134 has a square cross section (shape) having a side length 'L$_3$', and the second channel 136 has a round cross section (shape) equal of diameter 'D'. Herein, the first channel 134 and the second channel 136 are adapted to slidably receive components of the magnetic guide device 100 and thereby support such components and further allow to mount the ring 120 in the magnetic guide device 100. It may be appreciated that the dimensions, i.e., the side length 'L$_3$' and the diameter 'D', for the first channel 134 and the second channel 136 respectively may conform to the respective component received therein.

Figure 6A:
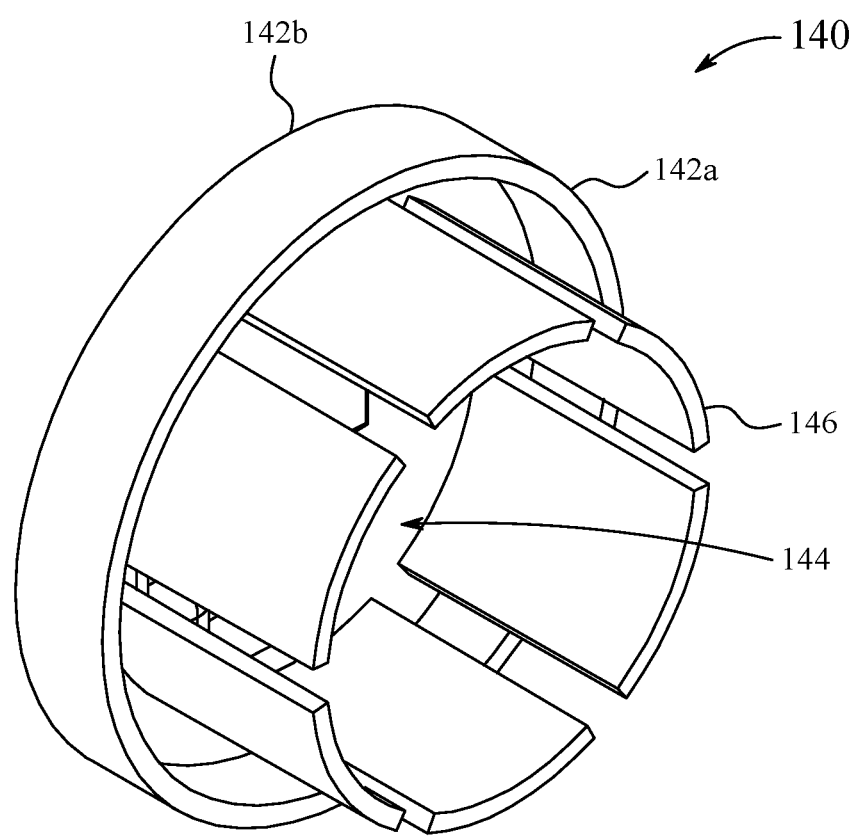
FIG. 6A is a perspective view of a rectangular collimator of the magnetic guide device, according to certain embodiments.
Figure 6B:
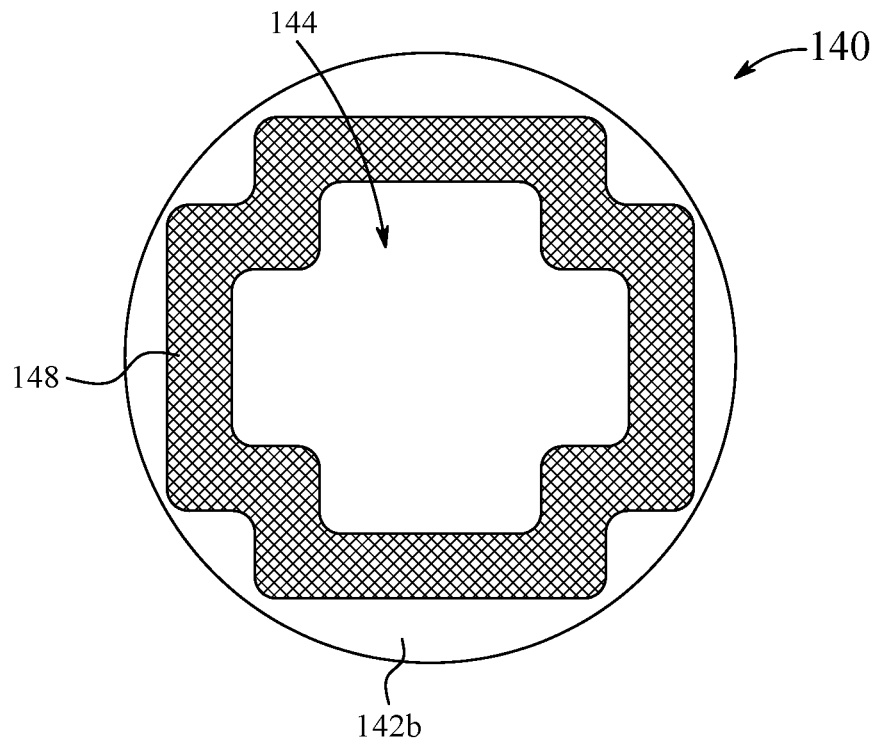
FIG. 6B is a planar view of a back side of the rectangular collimator, according to one embodiment.
Figure 6C:
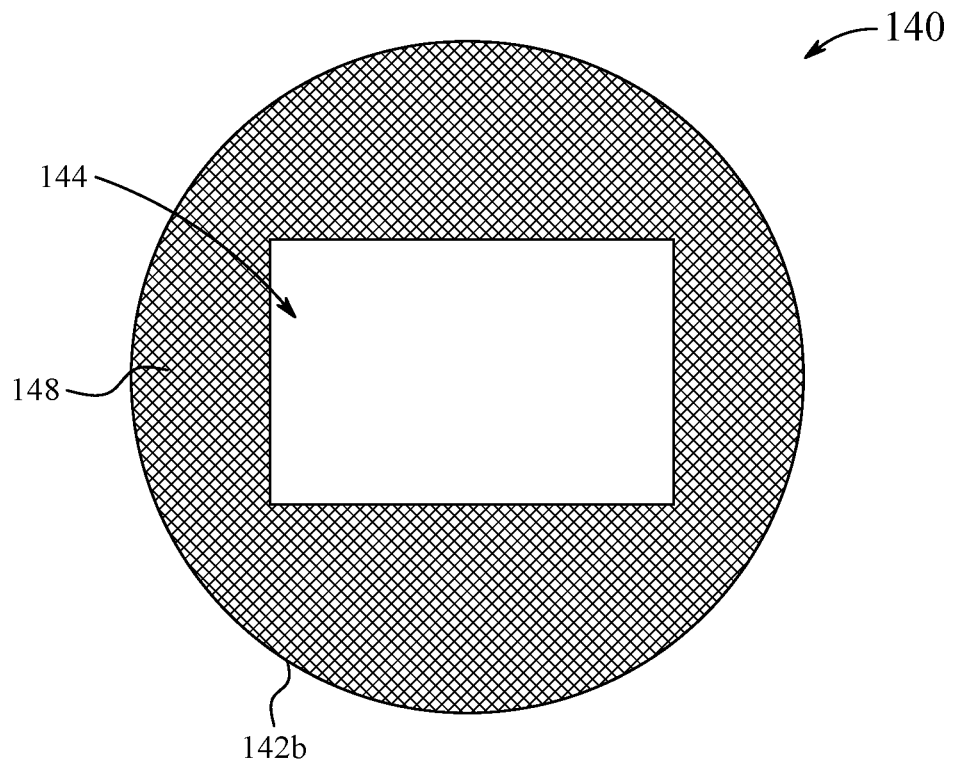
FIG. 6C is a planar view of a back side of the rectangular collimator, according to another embodiment.

Referring to FIGS. 1-3 in combination, as illustrated, the magnetic guide device 100 further includes a rectangular collimator 140 (hereinafter, referred to "collimator 140"). Further, FIGS. 6A-6C illustrate different views of the collimator 140. For the purposes of the present disclosure, the collimator 140 may alter a radiation output from a radiation source such that the radiation is substantially collimated or traveling largely or substantially in a single direction which may be parallel to a central axis of the collimator 140. The size and spread of the beam of radiation emanating from the radiation source, for example, the x-ray emitter tube, may be adjusted to any shape, for example, a substantially rectangular shape of varying sizes by the collimator 140. This may be desirable to align the radiation to be incident on a sensor (as discussed later) while minimizing scatter and excess radiation not used to expose the said sensor. As illustrated, the collimator 140 includes a front side 142*a* and a back side 142*b*. The collimator 140 further includes a rectangular opening 144 which extends through the collimator 140 from the front side 142*a* to the back side 142*b* thereof. The rectangular opening 144 is configured to pass x-rays (radiation) from the front side 142*a* to the back side 142*b*, of the collimator 140. As may be seen from FIG. 6A, the collimator 140 has a generally circular outer profile, and is being referred to as the rectangular collimator 140 due to the rectangular opening 144 therein collimating the radiation with a rectangular profile therefrom. Also, as illustrated, the collimator 140 includes a cylindrical extension 146 on the front side 142. As shown, the cylindrical extension 146 may be extending outwards from periphery of the circular profile of the collimator 140, in a direction opposite from the back side 142*b* in the collimator 140.

Referring specifically to FIGS. 6B and 6C, the back side 142*b* of the collimator 140 is shown according to two different aspects of the present disclosure. As illustrated, the rectangular collimator 140 further includes a magnetic material 148 configured to cover at least a portion of the back side 142*b*. In a non-limiting example, the magnetic material 148 may be a magnetic metal coating or magnetic metal sheet adhered to the back side of the collimator. Alternatively, the magnetic material may be a barium ferrite with appropriate magnetic polarity to complete the magnetic circuit through the magnetic attachments to the ring. Herein, the covered portion by the magnetic material 148 conforms to a periphery of the rectangular opening 144, in the collimator 140. In one aspect of the present disclosure, as illustrated in FIG. 6B, the covered portion of the back side 142*b* by the magnetic material 148 may have a shape complementary to the shape of the periphery 128 of the ring guide 124, i.e., similar to the cross shape of the periphery 128 of the ring guide 124. This may help to properly align the back side 142*b* of the collimator 140 with the periphery 128 of the ring guide 124, and thereby mount the collimator 140 to the ring 120 (as discussed later in the description). In another aspect of the present disclosure, as illustrated in FIG. 6C, the covered portion by the magnetic material 148 may be formed over entire surface area of the back side 142*b* of the collimator 140. This may allow the collimator 140 to be mounted to any other component of the magnetic guide device 100, such as the ring 120, with any suitable lateral alignment (as long as the rectangular opening 140 of the collimator 140 is aligned with the opening 126 in the ring guide 124 of the ring 120, for example, and as discussed later in the description).

Figure 7A:
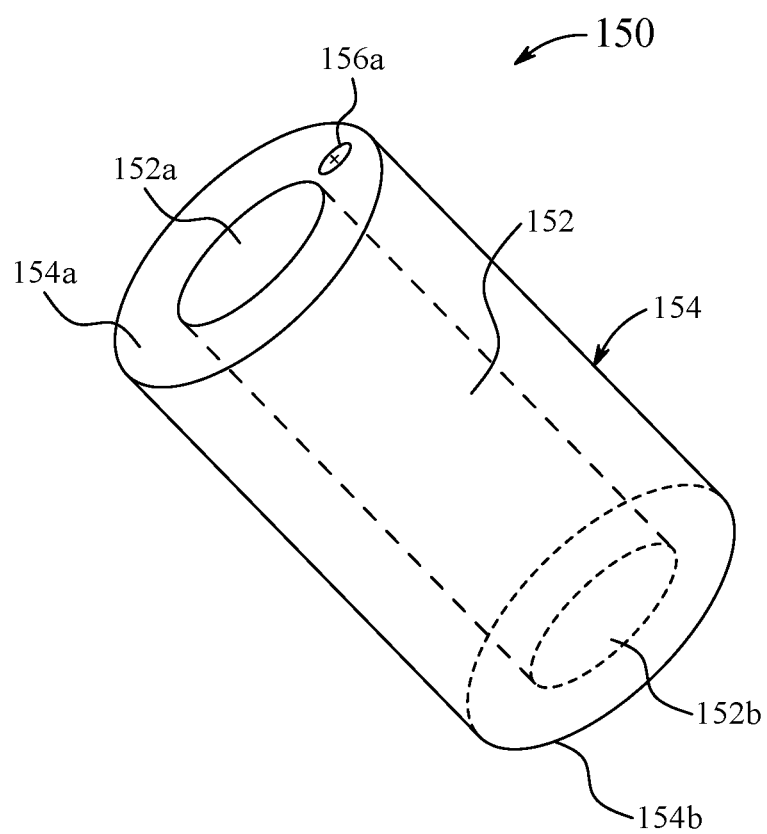
FIG. 7A is a perspective view of a magnetic attachment of the magnetic guide device, according to certain embodiments.
Figure 7B:
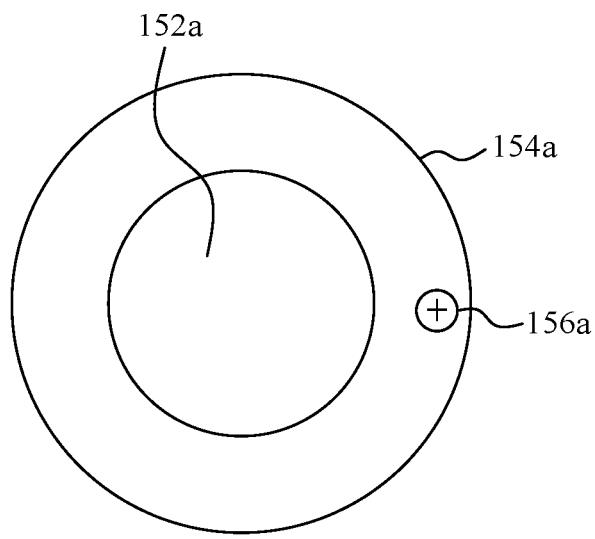
FIG. 7B is a planar view of a first face of the magnetic attachment, according to certain embodiments.
Figure 7C:
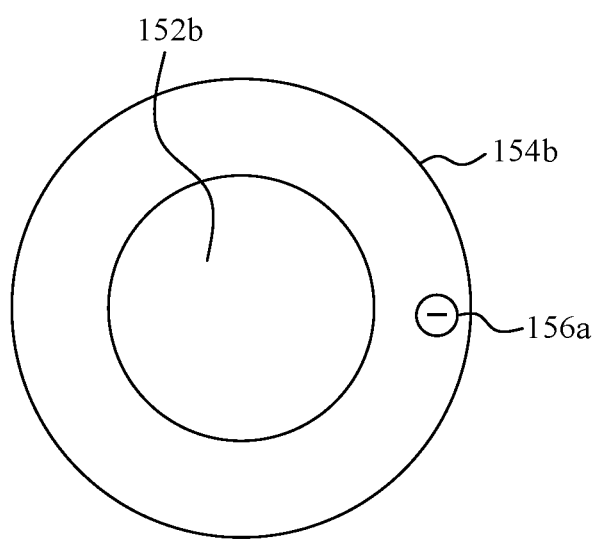
FIG. 7C is a planar view of a second face of the magnetic attachment, according to certain embodiments.
Figure 10:
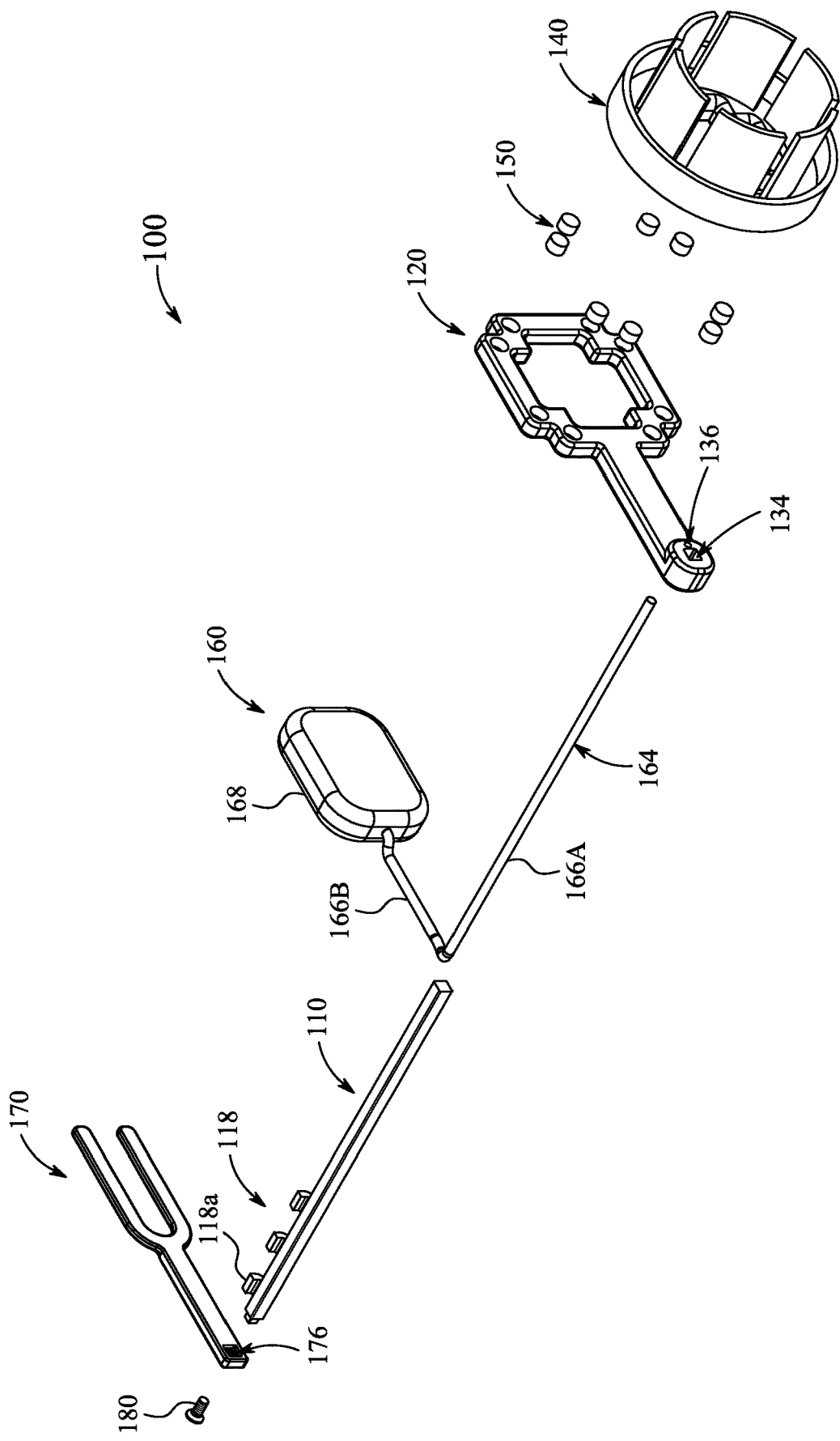
FIG. 10 is an exploded view of the magnetic guide device, according to certain embodiments.

Further, as may be seen from FIG. 3 and better seen in FIG. 10, the magnetic guide device 100 further comprises a plurality of magnetic attachments 150. Referring to FIGS. 7A-7C, illustrated are different views of the magnetic attachment 150, of the plurality of magnetic attachments 150. As illustrated, the magnetic attachment 150 generally has a cylindrical shape. In an aspect of the present disclosure, the magnetic guide device 100 includes a plurality of permanent magnets 152 (one shown in FIGS. 7A-7C). Each permanent magnet 152 has a positive magnetic pole 152*a* and a negative magnetic pole 152*b*. Further, the magnetic guide device 100 includes a closed cylindrical magnet housing 154 (as shown in FIGS. 7A-7C). The closed cylindrical magnet housing 154 has a first face 154*a* and a second face 154*b*. As may be seen from FIG. 7A, the closed cylindrical magnet housing 154 is configured to hold one of the permanent magnets 152. Specifically, the magnetic guide device 100 may have complementary number of magnet housings 154 to the permanent magnets 152, with each one of the magnet housings 154 holding one of the permanent magnets 152. Herein, the magnet housing 154 may have a hollow cylindrical profile to hold the permanent magnet 152 therein. As may be contemplated, the magnet housing 154 with the permanent magnet 152 held therein forms the magnetic attachment 150. That is, each magnetic attachment 150 contains one of the plurality of permanent magnets 152. In the present examples, the permanent magnet 152 is arranged in the magnet housing 154 such that the positive magnetic pole 152*a* of the permanent magnet 152 is disposed at the first face 154*a* of the closed cylindrical magnet housing 154 and the negative magnetic pole 152*b* of the permanent magnet 152 is disposed at the second face 154*b* of the closed cylindrical magnet housing 154. Further, as illustrated in FIGS. 7A-7C, in combination, the first face 154*a* of the closed cylindrical magnet housing 154 includes a positive magnetic pole indicator 156*a* (referring to the positive magnetic pole 152*a* of the permanent magnet 152) and the second face 154*b* of the closed cylindrical magnet housing 154 includes a negative magnetic pole indicator 156*b* (referring to the negative magnetic pole 152*b* of the permanent magnet 152).

In the present magnetic guide device 100, the rectangular collimator 140 is attached to the ring 120 by the magnetic attachments 150. In particular, the plurality of magnetic attachments 150 helps to magnetically couple the rectangular collimator 140 to the ring 120, by magnetically connecting to the magnetic material 148 on the back side 142*b* of the rectangular collimator 140 as well as the magnetic inserts 132 in the ring guide 124 of the ring 120. Herein, the positive magnetic pole 152*a* of the permanent magnet 152 is configured to magnetically bond to the magnetic material 148 on the back side 142*b* of the rectangular collimator 140; and the negative magnetic pole 152*b* of the permanent magnet 152 is configured to connect to the respective magnetic insert 132 of the ring 120. As may be contemplated, the plurality of magnetic attachments 150 may be equal in number to the number of the magnetic inserts 132, to have each one of the plurality of magnetic attachments 150 being magnetically connect to one of the magnetic inserts 132 of the ring 120. For instance, in the present examples, with the number of the magnetic inserts 132 being ten with four pairs, the number of magnetic attachments 150 is also equal to ten with corresponding four pairs, and have complementary alignment thereto, for providing such magnetic connection between the rectangular collimator 140 and the ring 120. In one or more aspects of the present disclosure, each magnetic insert 132 has a first magnetic pole (not shown); and attaching the magnetic attachment 150 to the magnetic insert 132 includes placing a second magnetic pole of the magnetic attachment 150 against the first magnetic pole of the magnetic insert 132, with the first magnetic pole and the second magnetic pole are opposite poles. That is, in case of the first magnetic pole of the magnetic insert 132 being a positive magnetic pole, the negative magnetic pole 152*b* would be the second magnetic pole of the magnetic attachment 150 and is attached to the first magnetic pole of the magnetic insert 132. Further, in some examples, an outer cylindrical surface 158 (as shown in FIG. 7A) of the closed cylindrical magnet housing 154 has a textured surface. Such textured surface of the outer cylindrical surface 158 of the magnet housing 154 for the magnetic attachment 150 helps to hold the magnetic attachment 150 in a cavity, like the insert cavity 130, by friction, for secure placement thereof.

Figure 8:
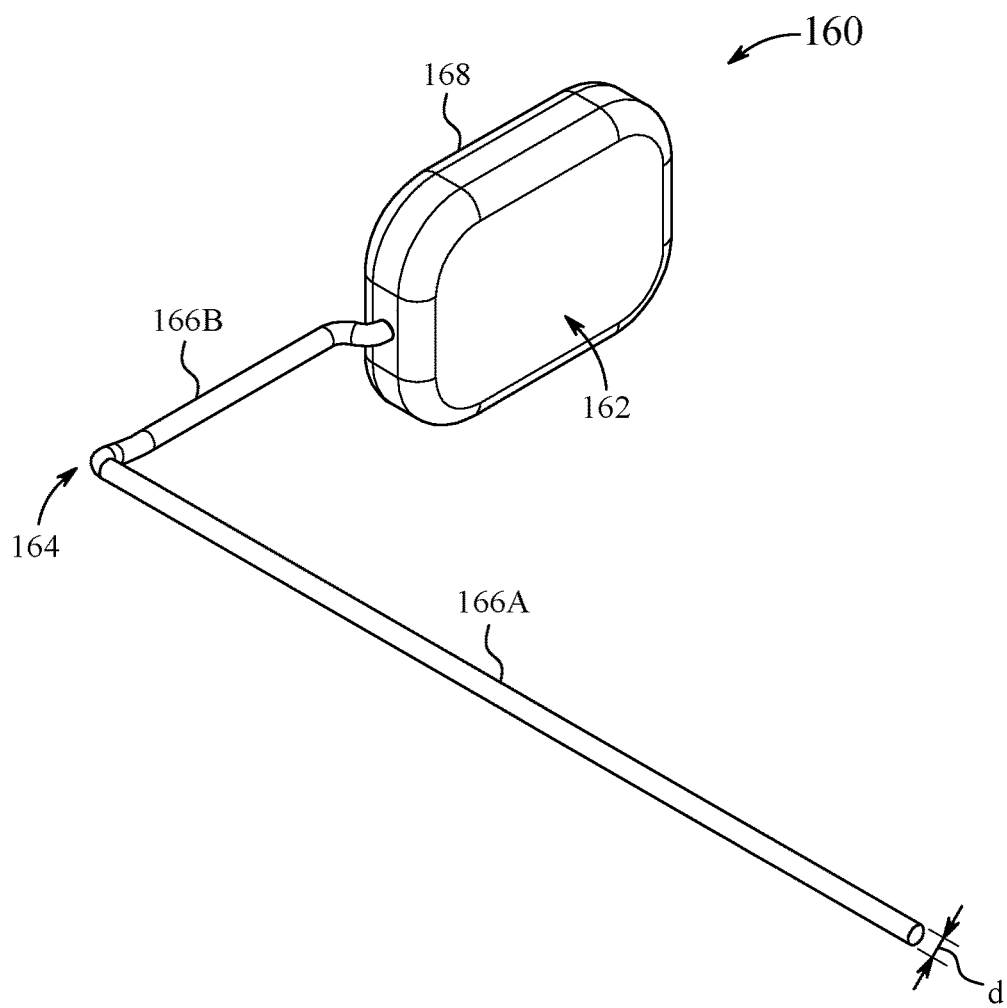
FIG. 8 is a perspective view of a CMOS sensor of the magnetic guide device, according to certain embodiments.

Referring to FIGS. 1-3 in combination, as illustrated, the magnetic guide device 100 further includes a CMOS sensor 160. As used herein, the term "CMOS sensor" may refer to complementary metal-oxide semiconductor sensor as known in the art in one example, but the term shall be construed to include any type of sensor suitable for intraoral radiography as used in dentistry, including, but not limited to, CCD, CMOS, flat panel detector, PSP imaging plate and the like. The CMOS sensor 160 is configured to receive the collimated radiation passed from the rectangular opening 144 of the collimator 140 to produce image of object, such a tooth in the oral cavity, located therebetween, when the CMOS sensor 160 of the magnetic guide device 100 is located in the oral cavity. FIG. 8 illustrates a perspective view of the CMOS sensor 160. In particular, as illustrated, the CMOS sensor 160 has a sensing region 162 configured to receive the collimated radiation. As shown, the sensing region 162 of the CMOS sensor 160 has a generally rectangular profile, which may complement to the rectangular opening 144 of the collimator 140. In some examples, the sensing region 162 may have dimensions generally equal to dimensions of the rectangular opening 144 of the collimator 140. Further, the CMOS sensor 160 includes a wire 164 coupled to the sensing region 162 therein. Herein, the wire 164 has a first portion 166A and a second portion 166B. As shown, in one or more examples, the wire 164 has a L-shaped profile (i.e., the wire 164 is bent), with the second portion 166B of the wire 164 being perpendicular to the first portion 166A of the wire 164. Further, in some examples, the magnetic guide device 100 includes a magnetic backing 168 (generally represented) located on the CMOS sensor 160. The magnetic backing 168 includes a magnetic material selected from the group comprising a magnetic coating, a magnetic metal sheet, a magnetic tape, and self-adhesive magnetic dots.

In an aspect of the present disclosure, the CMOS sensor 160 is mounted in the magnetic guide device 100 by supporting the wire 164 with the metal rod 110 and the ring 120. As may be understood from FIGS. 1-3 in combination, the plurality of wire guide clips 118 is configured to hold the first portion 166A of the wire 164 of the CMOS sensor 160 parallel to the metal rod 110. That is, the first portion 166A of the wire 164 of the CMOS sensor 160 may pass through and be received in the plurality of wire guide clips 118, to be disposed parallel to and supported by the metal rod 110. Further, the second channel 136 in the ring handle 122 is configured for receiving the first portion 166A of the wire 164 of the CMOS sensor 160. That is, the first portion 166A of the wire 164 of the CMOS sensor 160 passes through the second channel 136 in the ring handle 122 of the ring 120 to support the CMOS sensor 160 with the ring 120. In an example, the wire 164, or specifically the first portion 166A of the wire 164 may have a round cross section with a diameter, d, in a range of about 0.2 cm to 0.6 cm. Further, the second channel 136 which, as discussed, also has the round cross section to receive the first portion 166A of the wire 164 therein may have its diameter 'D' selected from a range consisting of 0.2 cm to 0.6 cm (generally equal to the range of diameter of the wire 164).

Figure 9:
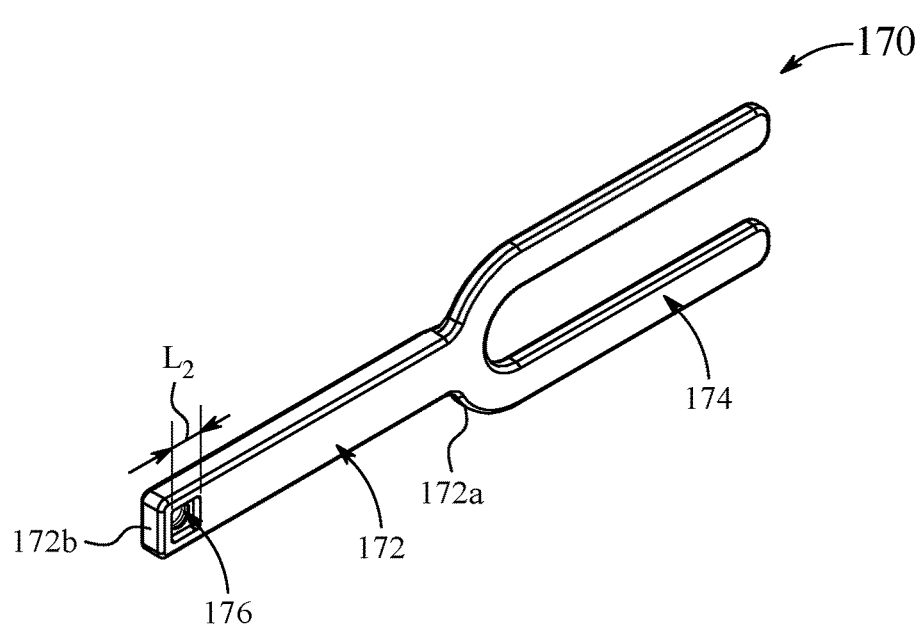
FIG. 9 is a perspective view of a metal fork of the magnetic guide device, according to certain embodiments.

Referring to FIGS. 1-3 in combination, as illustrated, the magnetic guide device 100 further includes a metal fork 170. FIG. 9 illustrates a perspective view of the metal fork 170. The metal fork 170 has a fork handle 172. Further, the fork handle 172 has a first fork handle end 172a and a second fork handle end 172b. The metal fork 170 further includes tines 174 therein. As shown, the first fork handle end 172a of the fork handle 172 is connected to the tines 174 in the metal fork 170. Herein, in one example, the fork handle 172 may be integrally formed with the tines 174, to form the metal fork 170. In other example, the fork handle 172 may be separately attached to the tines 174 by any suitable attachment method, like glue, welding, etc., to form the metal fork 170. Further, as better shown in FIG. 9, the second fork handle end 172b of the fork handle 172 includes a passage 176. Herein, the passage 176 is in the form of a square-shaped through-hole proximal to the second fork handle end 172b of the fork handle 172 in the metal fork 170. In the present configuration of the magnetic guide device 100, the passage 176 is configured for slidably receiving the metal rod 110 therein, and thereby the metal fork 170 is slidably attached to the metal rod 110 between the CMOS sensor 160 and the first rod end 112a of the metal rod 110. In present examples, as discussed, the metal rod 110 has the square cross section of side length '$L_1$', and, herein, the passage 176 also has a square cross section of side length '$L_2$'. The metal rod may be formed of a magnetic material, such as iron, so as to attach to the magnetic material on the back of the sensor.

Figure 11:
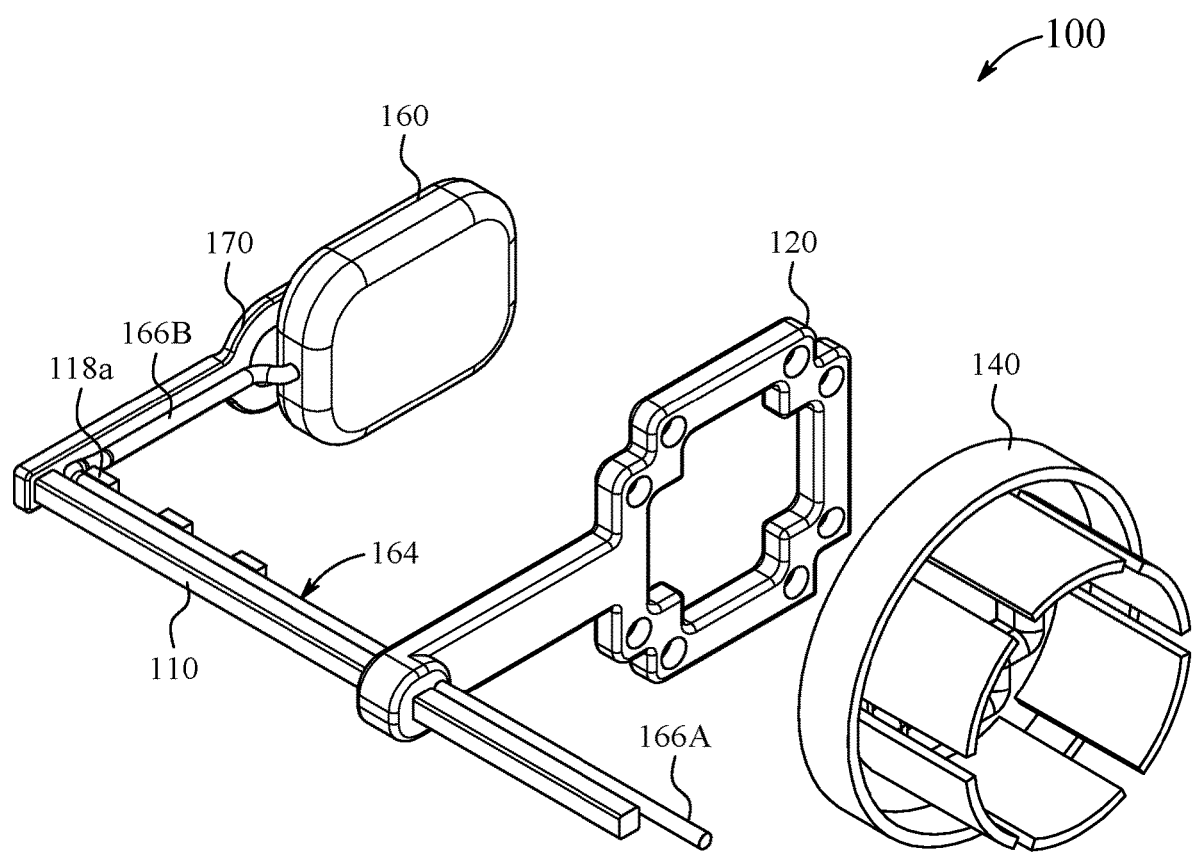
FIG. 11 is a partially exploded view of the magnetic guide device, according to certain embodiments.

Referring to FIG. 10, illustrated is a disassembled (exploded) view of the magnetic guide device 100. Further, referring to FIG. 11, illustrated is a partially assembled (partially exploded) view of the magnetic guide device 100. As illustrated in FIGS. 10 and 11, in the magnetic guide device 100, the metal fork 170 is configured to hold the CMOS sensor 160 during the intraoral radiography procedure. For this purpose, the magnetic guide device 100 may further include a screw 180 (as also shown in FIGS. 2 and 3). In the present examples, the screw 180 has male threads (not labelled). The screw 180 is configured for insertion through the passage 176 into female threads in the first rod end 112a of the metal rod 110 to engage with the male threads therein, such that the metal fork 170 compresses the second portion 166B of the wire 164 between the first wire guide clip 118a (as located on the metal rod 110) and the metal fork 170. Alternatively, the fork may be held to first end of the rod by a cap having internal threads which mate to threads on the first end of the rod, as described above. That is, the CMOS sensor 160 is sandwiched between the first wire guide clip 118a on the metal rod 110 and the metal fork 170. Furthermore, as discussed, the CMOS sensor 160 has the magnetic backing 168 located thereon. The magnetic backing 168 is configured to adjustably attract the metal fork 170 by magnetic forces, and thereby assist with mounting and holding the CMOS sensor 160 against the metal fork 170.

Also, as discussed, in the magnetic guide device 100, the first channel 134 in the ring handle 122 of the ring 120 is configured for slidably receiving the metal rod 110, in the magnetic guide device 100. For this purpose, the side length '$L_3$' of the first channel 134 is designed to be at least slightly greater than the side length '$L_1$' of the rod 110 to allow for the rod 110 to pass therethrough (as shown in FIG. 11). In an example, the side length $L_3 = L_1 x$, where $0 < x \leq 2$ mm. Further, the side length '$L_2$' of the passage 176 in the metal fork 170 is designed to be at least slightly greater than the side length '$L_1$' of the metal rod 110 to allow for the metal rod 110 to pass therethrough (as shown in FIG. 11). In an example, the side length $L_2 = L_1 + y$, where $0 < y \leq 2$ mm. Furthermore, as discussed, the wire 164, or specifically the first portion 166A of the wire 164 of the CMOS sensor 160 is received in the second channel 136 in the ring handle 122 of the ring 120. For this purpose, the diameter 'D' of the second channel 136 is designed to be at least slightly greater than the diameter 'd' of the first portion 166A of the wire 164.

Figure 12:
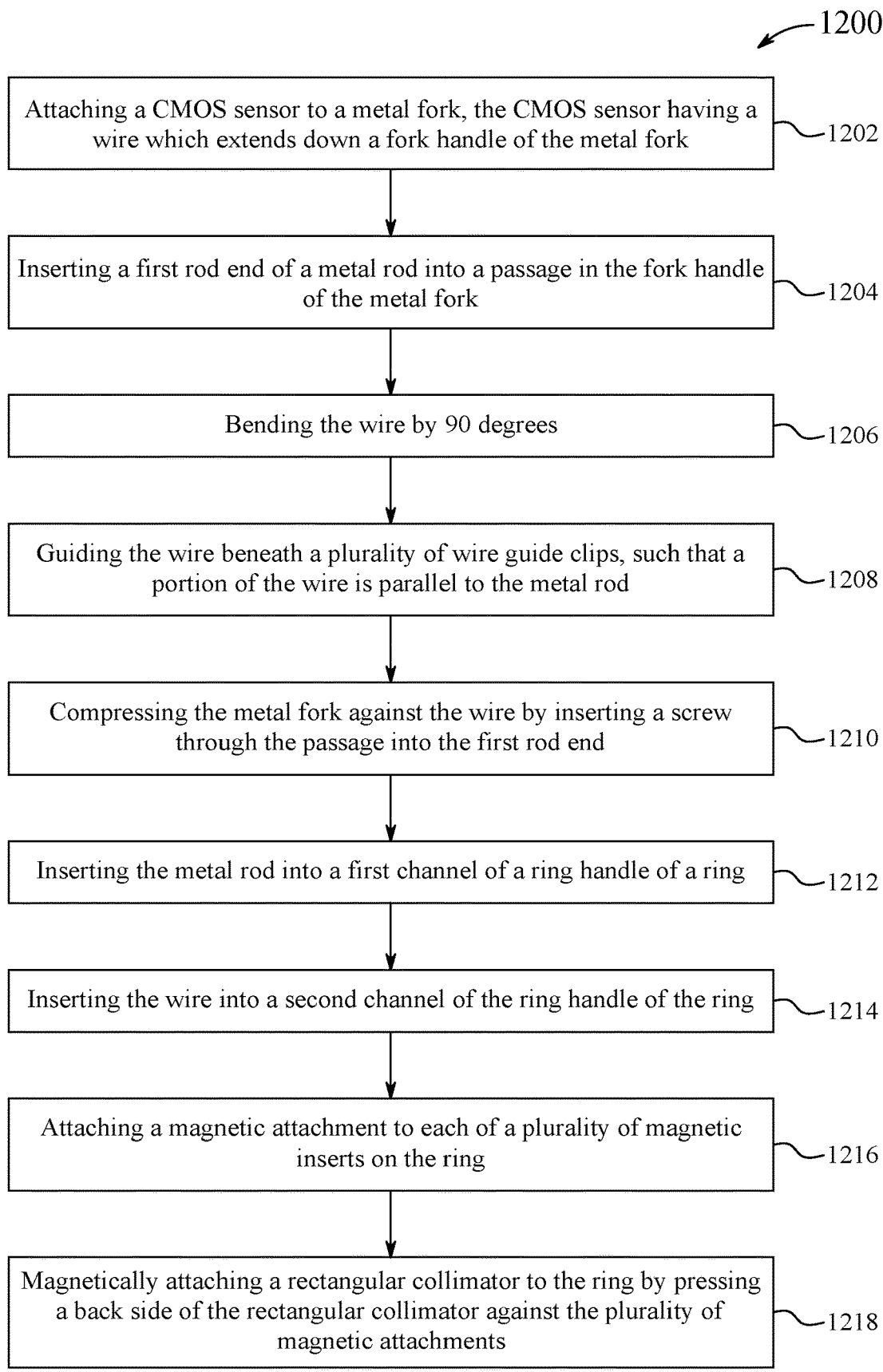
FIG. 12 is an exemplary flowchart of a method for assembling the magnetic guide device for intraoral radiography, according to certain embodiments.

Referring to FIG. 12, an exemplary flowchart of a method 1200 for assembling the magnetic guide device 100 for intraoral radiography is illustrated. The method 1200 is described with reference to the magnetic guide device 100 illustrated in FIG. 1 through FIG. 11. At step 1202, the method 1200 includes attaching the CMOS sensor 160 to the metal fork 170. Herein, the CMOS sensor 160 has the wire 164 which extends down the fork handle 172 of the metal fork 170. Herein, the CMOS sensor 160 is sandwiched between the first wire guide clip 118a on the metal rod 110 and the metal fork 170, and further the magnetic backing 168 assists with mounting and holding the CMOS sensor 160 against the metal fork 170. At step 1204, the method 1200 includes inserting the first rod end 112a of the metal rod 110 into the passage 176 in the fork handle 172 of the metal fork 170. Herein, with the side length '$L_2$' of the passage 176 being at least slightly greater than the side length '$L_1$' of the rod 110, this allows for the metal rod 110 to pass through the passage 176 in the metal fork 170. At step 1206, the method 1200 includes bending the wire 164 by 90 degrees. That is, the wire 164 is bent to define the first portion 166A and the second portion 166B thereof. At step 1208, the method 1200 includes guiding the wire 164 beneath the plurality of wire guide clips 118, such that a portion of the wire 164 is parallel to the metal rod 110. Herein, the plurality of wire guide clips 118 is configured to hold the first portion 166A of the wire 164 of the CMOS sensor 160 parallel to the metal rod 110. That is, the first portion 166A of the wire 164 of the CMOS sensor 160 may pass through and be received in the plurality of wire guide clips 118, to be disposed parallel to and supported by the metal rod 110. At step 1210, the method 1200 includes compressing the metal fork 170 against the wire 164 by inserting the screw 180 through the passage 176 into the first rod end 112a. Herein, the screw 180 is configured for insertion through the passage 176 into female threads in the first rod end 112a of the metal rod 110 to engage with the male threads therein, such that the metal fork 170 compresses the second portion 166B of the wire 164 between the first wire guide clip 118a (as located on the metal rod 110) and the metal fork 170. Thereby, the CMOS sensor 160 is supported between the first wire guide clip 118a on the metal rod 110 and the metal fork 170. At step 1212, the method 1200 includes inserting the metal rod 110 into the first channel 134 of the ring handle 122 of the ring 120. Herein, the first channel 134 is configured for slidably receiving the metal rod 110 of the magnetic guide device 100. At step 1214, the method 1200 includes inserting the wire 164 into the second channel 136 of the ring handle 122 of the ring 120. Herein, the first portion 166A of the wire 164 of the CMOS sensor 160 passes through the second channel 136 in the ring handle 122 of the ring 120 to support the CMOS sensor 160 with the ring 120. At step 1216, the method 1200 includes attaching the magnetic attachment 150 to each of the plurality of magnetic inserts 132 on the ring 120. Herein, with the plurality of magnetic attachments 150 being equal in number to the number of the magnetic inserts 132, each one of the plurality of magnetic attachments 150 is magnetically connected to one of the magnetic inserts 132 of the ring 120. At step 1218, the method 1200 includes magnetically attaching the rectangular collimator 140 to the ring 120 by pressing the back side 142b of the rectangular collimator 140 against the plurality of magnetic attachments 150. Herein, the plurality of magnetic attachments 150 helps to magnetically couple the rectangular collimator 140 to the ring 120, by magnetically connecting to the magnetic material 148 on the back side 142b of the rectangular collimator 140 as well as the magnetic inserts 132 in the ring guide 124 of the ring 120.

In one or more aspects of the present disclosure, the method 1200 further includes attaching each magnetic attachment 150 to one of the magnetic inserts 132 by one of placing the positive magnetic pole 152a of the magnetic attachment 150 against the magnetic insert 132; and placing the negative magnetic pole 152b of the magnetic attachment 150 against the magnetic insert 132. Herein, the positive magnetic pole 152a of the permanent magnet 152 is configured to magnetically bond to the magnetic material 148 on the back side 142b of the rectangular collimator 140; and the negative magnetic pole 152b of the permanent magnet 152 is configured to connect to the respective magnetic insert 132 of the ring 120.

In one or more aspects of the present disclosure, each magnetic insert has a first magnetic pole; and attaching the magnetic attachment 150 to the magnetic insert 132 comprises placing a second magnetic pole of the magnetic attachment 150 against the first magnetic pole 152a of the magnetic insert 132, wherein the first magnetic pole and the second magnetic pole are opposite poles. Herein, as discussed, in case of the first magnetic pole of the magnetic insert 132 being a positive magnetic pole (for instance), in such case the negative magnetic pole 152b would be the second magnetic pole of the magnetic attachment 150 and is attached to the first magnetic pole of the magnetic insert 132.

Figure 13:
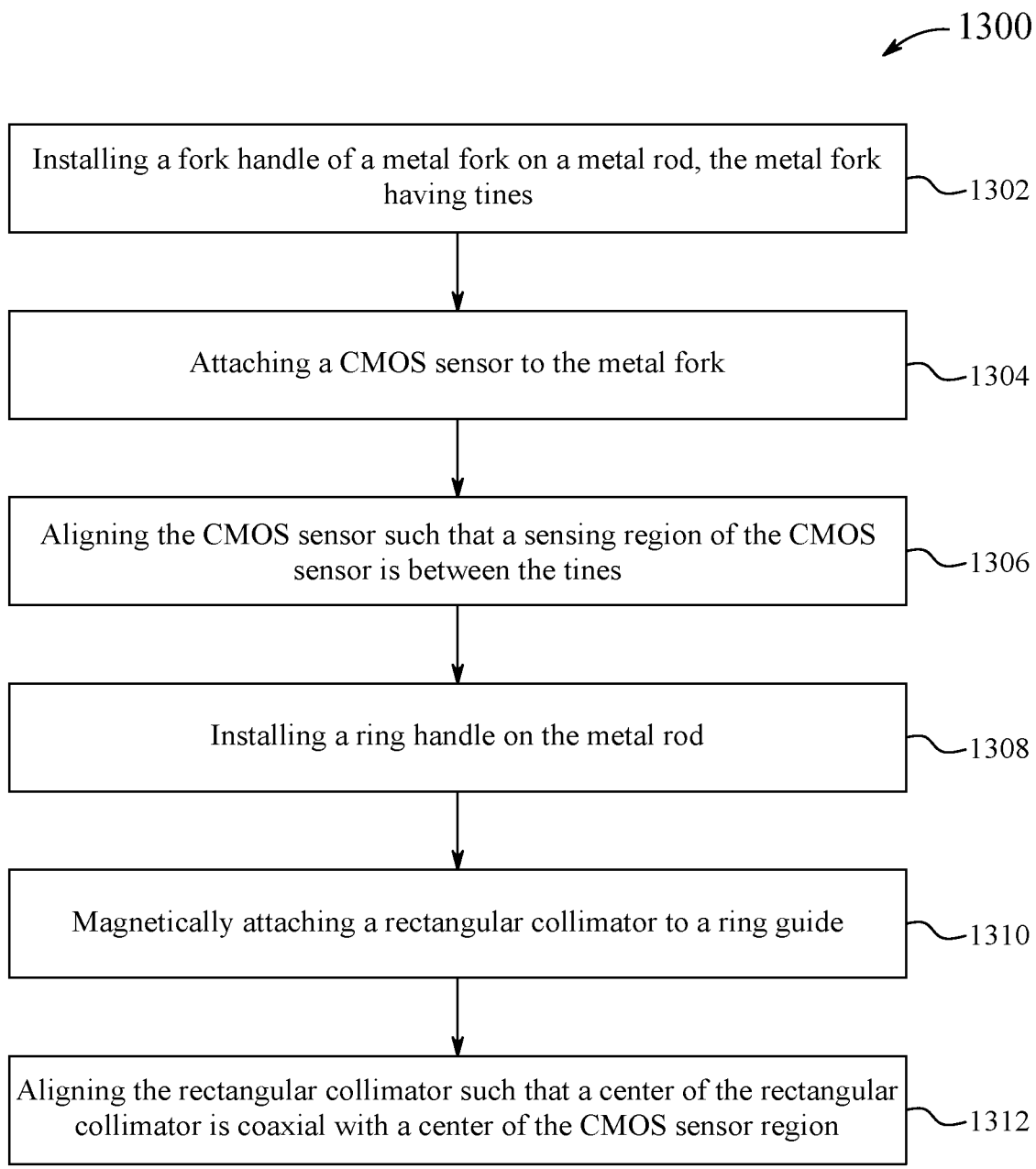
FIG. 13 is an exemplary flowchart of a method for aligning the magnetic guide device for intraoral radiography, according to certain embodiments.

Referring to FIG. 13, an exemplary flowchart of a method 1300 for aligning the magnetic guide device 100 for intraoral radiography is illustrated. The method 1300 is described with reference to the magnetic guide device 100 illustrated in FIG. 1 through FIG. 11. At step 1302, the method 1300 includes installing the fork handle 172 of the metal fork 170 on the metal rod 110, the metal fork 170 having tines 174. In the present configuration of the magnetic guide device 100, the passage 176 is configured for slidably receiving the metal rod 110 therein, and thereby the metal fork 170 is slidably attached to the metal rod 110 between the CMOS sensor 160 and the first rod end 112a of the metal rod 110. At step 1304, the method 1300 includes attaching the CMOS sensor 160 to the metal fork 170. As discussed, the magnetic backing 168 is configured to adjustably attract the metal fork 170 by magnetic forces, and thereby assist with mounting and holding the CMOS sensor 160 against the metal fork 170. At step 1306, the method 1300 includes aligning the CMOS sensor 160 such that the sensing region 162 of the CMOS sensor 160 is between the tines 174. That is, the CMOS sensor 160 is adjusted against the metal fork 170 with the sensing region 162 of the CMOS sensor 160 arranged between the tines 174. At step 1308, the method 1300 includes installing the ring handle 122 on the metal rod 110. For this purpose, the first channel 134 in the ring handle 122 of the ring 120 slidably receive the metal rod 110. With this configuration, the ring 120 is aligned with the CMOS sensor 160, in the magnetic guide device 100. At step 1310, the method 1300 includes magnetically attaching the rectangular collimator 140 to the ring guide 124. As discussed, the plurality of magnetic attachments 150 helps to magnetically couple the rectangular collimator 140 to the ring 120, by magnetically connecting to the magnetic material 148 on the back side 142b of the rectangular collimator 140 as well as the magnetic inserts 132 in the ring guide 124 of the ring 120. With this configuration, the rectangular opening 144 in the collimator 140 is aligned with the opening 126 in the ring guide 124 of the ring 120, and the rectangular collimator 140 is aligned to the ring 120, in the magnetic guide device 100. At step 1312, the method 1300 includes aligning the rectangular collimator 140 such that a center of the rectangular collimator 140 is coaxial with a center of the sensing region 162 of the CMOS sensor 160. As may be appreciated, with the CMOS sensor 160 being magnetically attached to the ring 120, it may be possible to detach, adjust an orientation of, and reattach the CMOS sensor 160 with respect to the ring 120, to cause the center of the rectangular collimator 140 being coaxial with the center of the sensing region 162 of the CMOS sensor 160.

The magnetic guide device 100 of the present disclosure provides adjustability through connections between its modular components that are easily snapped together with complementary connection features; and may also allow for using same modular components or different modular components, if needed. The present magnetic guide device 100 requires minimal assembly or adjustment during and/or just prior to actual operation to acquire images. The present magnetic guide device 100 further provides proper alignment of its components, to provide a substantially unobstructed line of sight between a radiation source, such as an existing X-ray emitter, and the CMOS sensor 160. The magnetic guide device 100 is capable of producing better quality images, reducing number of images required to be retaken, thus minimizing exposure of patients to unnecessary radiation.

The first embodiment of the present disclosure is illustrated with respect to FIG. 1 through FIG. 11. The embodiment describes the magnetic guide device 100 for intraoral radiography, comprising: the metal rod 110 having the first rod end 112a and the second rod end 112b; the ring 120 slidably attached to the metal rod 110 between the first rod end 112a and the second rod end 112b; the plurality of magnetic attachments 150; the rectangular collimator 160 attached to the ring 120 by the magnetic attachments 150; the CMOS sensor 160; and the metal fork 170 having the fork handle 172 slidably attached to the metal rod 110 between the CMOS sensor 160 and the first rod end 112a, wherein the metal fork 170 is configured to hold the CMOS sensor 160 during the intraoral radiography procedure.

The magnetic guide device 100, wherein the rectangular collimator 160 comprises: the front side 142a and the back side 142b; the cylindrical extension 146 on the front side 142a; the rectangular opening 144 which extends through the rectangular collimator 160 from the front side 142a to the back side 142b, the rectangular opening 144 configured to pass x-rays from the front side 142a to the back side 142b; and the magnetic material 148 configured to cover at least the portion of the back side 142b, wherein the portion conforms to the periphery of the rectangular opening 144.

The magnetic guide device 100, wherein the ring 120 comprises: the ring handle 122; and the ring guide 124 comprising the plurality of insert cavities 130 spaced around the periphery 128 of the ring guide 124, wherein each insert cavity 130 is configured to receive one of the plurality of magnetic inserts 132 such that each magnetic insert 132 is countersunk into one of the insert cavities 130.

The magnetic guide device 100, wherein each magnetic insert 132 comprises one of: the permanent magnet selected from the group comprising the neodymium iron boron (NdFeB) magnet, the samarium cobalt (SmCo) magnet, the alnico magnet, ceramic magnet, and the ferrite magnet; and the magnetic metal selected from the group comprising nickel, cobalt, steel, magnetic stainless steel, barium ferrite, and rare earth metals.

The magnetic guide device 100, further comprising: the plurality of permanent magnets 152, each permanent magnet 152 having the positive magnetic pole 152a and the negative magnetic pole 152b; wherein each magnetic attachment 150 contains one of the plurality of permanent magnets 152; and the positive magnetic pole 152a is configured to magnetically bond to the magnetic material 148 and the negative magnetic pole 152b is configured to connect to the respective magnetic insert 132 of the ring 120.

The magnetic guide device 100, further comprising: the closed cylindrical magnet housing 154 configured to hold one of the permanent magnets 152, wherein the outer cylindrical surface 158 of the closed cylindrical magnet housing 154 has the textured surface, the first face 154a of the closed cylindrical magnet housing 154 includes the positive magnetic pole indicator 156a and the second face 154b of the closed cylindrical magnet housing 154 includes the negative magnetic pole indicator 156b.

The magnetic guide device 100, wherein the ring handle 122 has the first ring handle end 122a and the second ring handle end 122b, wherein the first ring handle end 122a is connected to the ring guide 124, and the second ring handle end 122b includes the first channel 134 configured for slidably receiving the metal rod 110 and the second channel 136 configured for receiving the first portion 166A of the wire 164 of the CMOS sensor 160.

The magnetic guide device 100, wherein the fork handle 172 has the first fork handle end 172a and the second fork handle end 172b, wherein the first fork handle end 172a is connected to the metal fork 170, and the second fork handle end 172b includes the passage 176 configured for slidably receiving the metal rod 110.

The magnetic guide device 100, further comprising: the plurality of wire guide clips 118 attached to the metal rod 110 between the CMOS sensor 160 and the ring 120, wherein the plurality of wire guide clips 118 is configured to hold the first portion 166A of the wire 164 parallel to the metal rod 110.

The magnetic guide device 100, wherein the plurality of wire guide clips 118 comprises at least the first wire guide clip 118a, the second wire guide clip 118b and the third wire guide clip 118c, wherein: the first wire guide clip 118a is spaced from the first rod end 112a of the metal rod 110 by the distance $R_1$; the second wire guide clip 118b is spaced from the first rod end 112a of the metal rod 110 by the distance $R_2$; the third wire guide clip 118c is spaced from the first rod end 112a of the metal rod 110 by the distance $R_3$, where $R_1<R_2<R_3$; and the third wire guide clip 118c is further configured to stop the ring handle 122 from sliding past the third wire guide clip 118c towards the first rod end 112a.

The magnetic guide device 100, further comprising: the screw 180 having male threads, wherein the screw 180 is configured for insertion through the passage 176 into female threads in the first rod end 112a of the metal rod 110, such that the metal fork 170 compresses the second portion 166B of the wire 164 between the first wire guide clip 118a and the metal fork 170.

The magnetic guide device 100, wherein the second portion 166B of the wire 164 is perpendicular to the first portion 166A of the wire 164.

The magnetic guide device 100, wherein the metal rod 110 has the square cross section of side length L1 and the passage 176 has the square cross section of side length $L_2$, wherein $L_2=L_1+y$, where $0<y\leq 2$ mm.

The magnetic guide device 100, wherein the first channel 134 has the square cross section having the side length $L_2$, and the second channel 136 has the round cross section equal of diameter D is selected from the range consisting of 0.2 cm to 0.6 cm.

The magnetic guide device 100, further comprising; the magnetic backing 168 located on the CMOS sensor 160, the magnetic backing 168 comprising the magnetic material selected from the group comprising the magnetic coating, the magnetic metal sheet, the magnetic tape, and self-adhesive magnetic dots, wherein the magnetic backing 168 is configured to adjustably attract the metal fork 170 by magnetic forces.

The second embodiment of the present disclosure is illustrated with respect to FIG. 1 to FIG. 12. The method 1200 for assembling the magnetic guide device 100 for intraoral radiography, comprising: attaching the CMOS sensor 160 to the metal fork 170, the CMOS sensor 160 having the wire 164 which extends down the fork handle 172 of the metal fork 170; inserting the first rod end 112*a* of the metal rod 110 into the passage 176 in the fork handle 172 of the metal fork 170; bending the wire 164 by 90 degrees; guiding the wire 164 beneath the plurality of wire guide clips 118, such that the portion of the wire 164 is parallel to the metal rod 110; compressing the metal fork 170 against the wire 164 by inserting the screw 180 through the passage 176 into the first rod end 112*a*; inserting the metal rod 110 into the first channel 134 of the ring handle 122 of the ring 120; inserting the wire 164 into the second channel 136 of the ring handle 122 of the ring 120; attaching the magnetic attachment 150 to each of the plurality of magnetic inserts 132 on the ring 120; and magnetically attaching the rectangular collimator 160 to the ring 120 by pressing the back side 142*b* of the rectangular collimator 160 against the plurality of magnetic attachments 150.

The method 1200, further comprising: attaching each magnetic attachment 150 to one of the magnetic inserts 132 by one of: placing the positive magnetic pole 152*a* of the magnetic attachment 150 against the magnetic insert 132; and placing the negative magnetic pole 152*b* of the magnetic attachment 150 against the magnetic insert 132.

The method 1200, wherein: each magnetic insert 132 has the first magnetic pole; and attaching the magnetic attachment 150 to the magnetic insert 132 comprises placing the second magnetic pole of the magnetic attachment 150 against the first magnetic pole of the magnetic insert 132, wherein the first magnetic pole and the second magnetic pole are opposite poles.

The third embodiment of the present disclosure is illustrated with respect to FIG. 1 to FIG. 13. The method 1300 for aligning the magnetic guide device 100 for intraoral radiography, comprising: installing the fork handle 172 of the metal fork 170 on the metal rod 110, the metal fork 170 having tines; attaching the CMOS sensor 160 to the metal fork 170; aligning the CMOS sensor 160 such that the sensing region of the CMOS sensor 160 is between the tines; installing the ring handle 122 on the metal rod 110; magnetically attaching the rectangular collimator 160 to the ring guide 124; and aligning the rectangular collimator 160 such that the center of the rectangular collimator 160 is coaxial with the center of the sensing region of the CMOS sensor 160.

The method 1300, further comprising: adjusting the distance between the rectangular collimator 160 and the CMOS sensor 160 by moving the ring handle 122 one of towards the CMOS sensor 160 and away from the CMOS sensor 160.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A magnetic guide device for intraoral radiography, comprising:
   a metal rod having a first rod end and a second rod end;
   a ring having a ring handle that is slidably attached to the metal rod between the first rod end and the second rod end;
   a plurality of magnetic attachments;
   a rectangular collimator attached to the ring by the plurality of magnetic attachments;
   wherein the rectangular collimator comprises:
   a front side and a back side;
   a cylindrical extension on the front side;
   wherein the cylindrical extension is segmented having at least 4 segments,
   wherein the segments are configured to compress when inserted into an x-ray source,
   a cross shaped opening which extends through the rectangular collimator from the front side to the back side, the cross shaped opening configured to pass x-rays from the front side to the back side; and
   a magnetic material configured to cover at least a portion of the back side,
   wherein the portion conforms to a periphery of the cross shaped opening,
   a CMOS sensor having a wire; and
   a metal fork having a fork handle slidably attached to the metal rod between the CMOS sensor and the first rod end, wherein the metal fork is configured to hold the CMOS sensor during an intraoral radiography procedure,
   wherein the ring handle has a first ring handle end and a second ring handle end, wherein the first ring handle end is connected to a ring guide, and the second ring handle end includes a first channel configured for slidably receiving the metal rod and a second channel configured for receiving a first portion of the wire of the CMOS sensor,
   wherein the wire of the CMOS sensor is parallel to and in physical contact with the metal rod.

2. The magnetic guide device of claim 1, wherein the ring guide comprises:
   a plurality of insert cavities spaced around a periphery of the ring guide, wherein each insert cavity is configured to receive one of a plurality of magnetic inserts such that each magnetic insert is countersunk into one of the insert cavities.

3. The magnetic guide device of claim 2, wherein each magnetic insert comprises one of:
   a permanent magnet selected from the group comprising a neodymium iron boron (NdFeB) magnet, a samarium cobalt (SmCo) magnet, an alnico magnet, ceramic magnet, and a ferrite magnet; and
   a magnetic metal selected from the group comprising nickel, cobalt, steel, magnetic stainless steel, barium ferrite, and rare earth metals.

4. The magnetic guide device of claim 2, further comprising:
   a plurality of permanent magnets, each permanent magnet having a positive magnetic pole and a negative magnetic pole;
   wherein each magnetic attachment contains one of the plurality of permanent magnets; and
   the positive magnetic pole is configured to magnetically bond to the magnetic material and the negative magnetic pole is configured to connect to a respective magnetic insert of the ring.

5. The magnetic guide device of claim 4, further comprising:
   a closed cylindrical magnet housing configured to hold one of the plurality of permanent magnets, wherein an outer cylindrical surface of the closed cylindrical magnet housing has a textured surface, a first face of the closed cylindrical magnet housing includes a positive magnetic pole indicator and a second face of the closed cylindrical magnet housing includes a negative magnetic pole indicator.

6. The magnetic guide device of claim 1, wherein the fork handle has a first fork handle end and a second fork handle end, wherein the first fork handle end is connected to the metal fork, and the second fork handle end includes a passage configured for slidably receiving the metal rod.

7. The magnetic guide device of claim 6, further comprising:
   a plurality of wire guide clips attached to the metal rod between the CMOS sensor and the ring, wherein the plurality of wire guide clips is configured to hold the first portion of the wire parallel to the metal rod.

8. The magnetic guide device of claim 7, wherein the plurality of wire guide clips comprises at least a first wire guide clip, a second wire guide clip and a third wire guide clip, wherein:
   the first wire guide clip is spaced from the first rod end of the metal rod by a distance $R_1$;
   the second wire guide clip is spaced from the first rod end of the metal rod by a distance $R_2$;
   the third wire guide clip is spaced from the first rod end of the metal rod by a distance $R_3$, where $R_1<R_2<R_3$; and
   the third wire guide clip is further configured to stop the ring handle from sliding past the third wire guide clip towards the first rod end.

9. The magnetic guide device of claim 8, further comprising:
   a screw having male threads, wherein the screw is configured for insertion through the passage into female threads in the first rod end of the metal rod, such that the metal fork compresses a second portion of the wire between the first wire guide clip and the metal fork.

10. The magnetic guide device of claim 9, wherein the second portion of the wire is perpendicular to the first portion of the wire.

11. The magnetic guide device of claim 6, wherein the metal rod has a square cross section of side length $L_1$ and the passage has a square cross section of side length $L_2$, wherein $L_2=L_1$ y, where $0<y\leq2$ mm.

12. The magnetic guide device of claim 11, wherein the first channel has a square cross section having side length $L_2$, and the second channel has a round cross section equal of diameter D is selected from a range consisting of 0.2 cm to 0.6 cm.

13. The magnetic guide device of claim 1, further comprising;
   a magnetic backing located on the CMOS sensor, the magnetic backing comprising a magnetic material selected from the group comprising a magnetic coating, a magnetic metal sheet, a magnetic tape, and self-adhesive magnetic dots, wherein the magnetic backing is configured to adjustably attract the metal fork by magnetic forces.

* * * * *